United States Patent
Domankevitz et al.

(10) Patent No.: US 6,350,261 B1
(45) Date of Patent: Feb. 26, 2002

(54) SELECTIVE LASER-INDUCED HEATING OF BIOLOGICAL TISSUE

(75) Inventors: Yacov Domankevitz, Brookline; R. Rox Anderson, Lexington, both of MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 09/547,299

(22) Filed: Apr. 11, 2000

Related U.S. Application Data

(63) Continuation-in-part of application No. 09/132,878, filed on Aug. 11, 1998, now Pat. No. 6,126,655.

(51) Int. Cl.[7] .............................................. A61B 18/18
(52) U.S. Cl. ................................................ 606/17; 606/9
(58) Field of Search ................................. 606/9, 13–17, 606/1–2, 5; 607/89

(56) References Cited

U.S. PATENT DOCUMENTS

| | | |
|---|---|---|
| 4,122,342 A | 10/1978 | Vali et al. |
| 4,273,127 A | 6/1981 | Auth et al. |
| 4,387,954 A | 6/1983 | Beasley |
| 4,400,056 A | 8/1983 | Cielo |
| 4,447,546 A | 5/1984 | Hirschfeld |
| 4,585,298 A | 4/1986 | Mori |
| 4,660,925 A | 4/1987 | McCaughan, Jr. |
| 4,672,961 A | 6/1987 | Davies |
| 4,693,244 A | 9/1987 | Daikuzono |
| 4,707,201 A | 11/1987 | Failes |
| 4,712,543 A | 12/1987 | Baron |
| 4,799,479 A | 1/1989 | Spears |
| 4,852,567 A | 8/1989 | Sinofsky |
| 4,911,712 A | 3/1990 | Harrington |
| 5,018,842 A | 5/1991 | Chen |
| 5,042,980 A | 8/1991 | Baker et al. |
| 5,122,060 A | 6/1992 | Vassiliadis et al. |
| 5,139,495 A | 8/1992 | Daikuzono |
| 5,190,538 A * | 3/1993 | Hussein et al. ............ 606/17 |
| 5,207,669 A | 5/1993 | Baker et al. |
| 5,248,311 A | 9/1993 | Black et al. |
| 5,254,114 A | 10/1993 | Reed, Jr. et al. |

(List continued on next page.)

FOREIGN PATENT DOCUMENTS

| | | |
|---|---|---|
| EP | 0 400802 A2 | 12/1990 |
| EP | 0 529 823 | 3/1993 |
| GB | 2 154761 A | 9/1985 |
| GB | 2 222881 A | 3/1990 |
| WO | WO91/02562 | 3/1991 |
| WO | WO95/17924 | 7/1995 |

OTHER PUBLICATIONS

Cox, Jr., "New Method for Exposing Mammalian Cells to Intense Laser Radiation Using the Evanescent Fields Created in Optical Waveguides," *Am. Assoc. Phys. Med.*, 5:274–279, Jul./Aug. 1978.

Prince et al., "Preferential Ablation of Calcified Arterial Plaque with Laser–Induced Plasmas," *IEEE Journal of Quantum Electronics*, QE23:1783–1786, Oct. 1987.

Primary Examiner—Roy Gibson
(74) Attorney, Agent, or Firm—Fish & Richardson P.C.

(57) ABSTRACT

The invention features methods and systems for selectively delivering or coupling laser radiation into a first material or substrate, e.g., a first biological tissue, having a first index of refraction and not into a second material or substrate, e.g., a second biological tissue, having a second index of refraction. The system determines whether a target area corresponds to the first material or the second material by monitoring the reflection of a probe beam incident on the target area through an optical coupler at a non-normal incident angle. The monitored reflection of the probe beam is a control signal for a feedback controller that causes a treatment beam to be delivered to the target area based on the monitored reflection.

42 Claims, 11 Drawing Sheets

U.S. PATENT DOCUMENTS

| | | |
|---|---|---|
| 5,342,352 A | 8/1994 | Franken et al. |
| 5,380,318 A | 1/1995 | Daikuzono |
| 5,496,309 A * | 3/1996 | Saadat et al. .................. 606/15 |
| 5,498,260 A | 3/1996 | Rink et al. |
| 5,534,000 A | 7/1996 | Bruce |
| 5,707,368 A | 1/1998 | Cozean et al. |
| 5,833,683 A * | 11/1998 | Fuller et al. .................. 606/17 |

* cited by examiner

SELECTIVE LASER-INDUCED HEATING OF BIOLOGICAL TISSUE

CROSS-REFERENCE TO RELATED APPLICATIONS

This application is a continuation-in-part of U.S. patent application Ser. No. 09/132,878, now U.S. Pat. No. 6,126,655, by Yacov Domankevitz and R. Rox Anderson, filed on Aug. 11, 1998 and entitled "Apparatus and Method for Selective Laser-Induced Heating of Biological Tissue," which is incorporated herein in its entirety.

BACKGROUND OF THE INVENTION

Lasers are useful in medical, materials processing, and other applications to cause ablation, i.e., substance removal, within a substrate, e.g., a biological tissue. In many cases, lasers cause such ablation by rapidly and locally heating a target substance until the target substance vaporizes.

Selective laser ablation can be accomplished by using laser wavelengths that are strongly absorbed by the target tissue and only weakly absorbed by other tissue. Thus, the target tissue absorbs an amount of laser energy above a threshold for laser ablation and is removed, whereas the other tissue absorbs an amount of laser energy below the threshold and remains. However, few medical lasers and delivery systems currently available operate at wavelengths that are absorbed substantially more by some types of tissue and not by other types of tissue.

SUMMARY OF THE INVENTION

The invention features a system for selectively delivering or coupling laser radiation into a first material or substrate, e.g., a first biological tissue, having a first index of refraction and not into a second material or substrate, e.g., a second biological tissue, having a second index of refraction. The system determines whether a target area corresponds to the first material or the second material by monitoring the reflection of a probe beam incident on the target area through an optical coupler at a non-normal incident angle. For example, the incident angle can be less than the critical angle for total internal reflection for an interface between the optical coupler and the first material, and greater than the critical angle for total internal reflection for an interface between the optical coupler and the second material, in which case transmission of the probe beam is much greater when the optical coupler contacts the first material than when the optical coupler contacts the second material, and similarly, reflection of the probe beam is much greater when the optical coupler contacts the second material than when the optical coupler contacts the first material, with respect to reflection. The monitored reflection of the probe beam is the control signal for a feedback controller that causes a treatment beam to be delivered to the target area based on the monitored reflection. Thus, the control system selectively delivers the treatment beam to the target area when the optical coupler for the probe beam contacts the first material, but not the second material, or vice versa.

The treatment beam is at a wavelength and has sufficient energy to cause photophysical or photochemical change at the target area. For example, the treatment beam can be used to selectively remove fat-containing tissue from a target area. Fat-removal can be important in procedures such as laser liposuction, laser angioplasty, and dissection of fat. The laser energy delivered to the selected tissue by the treatment beam can rapidly heat the selected tissue until it vaporizes, thereby removing, ablating, or killing the selected tissue. Alternatively, the laser radiation delivered to the selected tissue can rapidly heat the selected tissue until it melts. Thereafter, the melted tissue is removed using suction or other methods.

Furthermore, rather than having an active feedback control system in which reflection of a probe beam incident on the target area at a non-normal angle controls the delivery of a treatment beam to the target area, the treatment beam itself can be delivered to the target area (though an optical coupler) at a non-normal incident angle. The incident angle is selected such that the treatment beam substantially reflects from the target area if the tissue therein is a first type of material (e.g., muscle-containing tissue) having a first refractive index and substantially couples into the target area if the tissue therein is a second type of material (e.g., fat-containing tissue) having a second refractive index greater than the first refractive index. In such examples, the treatment beam functions as both a probe beam selectively coupling into one type of material and not another, and a treatment beam causing photophysical or photochemical change when coupling into a material. Thus, the invention features both active and passive control systems for selectively delivering or coupling laser radiation into a first material or substrate and not a second material or substrate.

In general, in one aspect, the invention features a method for selectively delivering a treatment beam to portions of a substrate having a first index of refraction and not to other portions of the substrate having a second index of refraction less than the first index. The method includes: providing an optical coupler having an index of refraction greater than the second index of refraction; contacting the substrate with the optical coupler to deliver a probe beam from the optical coupler to the substrate at an incident angle; and selectively delivering the treatment beam to the region based on the reflectance of the probe beam from the substrate or the transmission of the probe beam through the substrate.

The method can include any of the following features.

The incident angle can be less than the critical angle for an interface between the optical coupler and a material having the first index of refraction and greater than the critical angle for an interface between the optical coupler and a material having the second index of refraction. The incident angle can be greater than about 10°, 20°, 30°, or 40°. The incident angle can be selected such that when the probe beam is incident on the substrate at the incident angle, the reflectance of the probe beam from an interface between the optical coupler and the portions of the substrate having the first index is at least twice, or at least four times, the reflectance of the probe beam from an interface between the optical coupler and the portions of the substrate having the second index. The optical coupler can have an index of refraction greater than the first index of refraction.

The treatment beam can have a wavelength different than that of the probe beam. The treatment beam can have a power greater than that of the probe beam. The substrate can absorb more strongly at the wavelength of the treatment beam than at the wavelength of the probe beam. The treatment beam can be delivered to the substrate through the optical coupler. The treatment beam can be selectively delivered to the region based on the reflectance of the probe beam from the substrate. For example, the treatment beam can be delivered to the region when the reflectance is less than about 0.95, less than about 0.9, less than about 0.8, or less than about 0.7.

The substrate can be biological tissue. For example, the portions of the substrate having the first index can include fat, e.g., they can consist essentially of fat. Alternatively, or in addition, portions of the substrate having the second index can include one or more of muscle, blood vessels, and skin, e.g., they can consist essentially of one of muscle, blood vessels, and skin. The power of the treatment beam can be sufficient to melt or ablate the portions of the substrate having the first index, and it can be delivered to the substrate at normal incidence. Each of the probe and treatment beams can be derived from a Nd:YAG laser, CTE:YAG laser, ErCr:YSGG laser, holmium laser, erbium laser, $CO_2$ laser, diode laser, or dye laser. The probe beam can also be derived from a light emitting diode. The optical coupler can be made from one of sapphire, fused silica, BK-7 glass, fint glass, germanium, and zinc selenide.

In another aspect, the invention features a system for selectively delivering a treatment beam to portions of a substrate having a first index of refraction and not to other portions of the substrate having a second index of refraction less than the first index. The system includes: an optical coupler having a surface configured to contact the substrate and a refractive index greater than the second index; a probe beam source configured to direct a probe beam into the optical coupler to contact the surface at an incident angle; a detector configured to measure the reflectance of the probe beam from the surface or the transmission of the probe beam through the surface; a treatment beam source for the treatment beam; and a controller which during operation causes the treatment beam source to selectively deliver the treatment beam to the substrate based on the reflectance or transmission measured by the detector.

The system can include any of the following features.

The incident angle can be less than the critical angle for an interface between the optical coupler and a material having the first index of refraction and greater than the critical angle for an interface between the optical coupler and a material having the second index of refraction. For example, the incident angle can be less than the critical angle for an interface between the optical coupler and a material consisting essentially of fat and greater than the critical angle for an interface between the optical coupler and another material consisting essentially of one of muscle, blood vessels, and skin. The incident angle can be greater than about 10°, 20°, 30°, or 40°.

The incident angle can be selected such that when the probe beam is incident on the surface of the optical coupler configured to contact the substrate at the incident angle, the reflectance of the probe beam from an interface between the optical coupler and the portions of the substrate having the first index is at least twice, or at least four times the reflectance of the probe beam from an interface between the optical coupler and the portions of the substrate having the second index. For example, the incident angle can be selected such that when the probe beam is incident on the surface of the optical coupler configured to contact the substrate at the incident angle, the reflectance of the probe beam from an interface between the optical coupler and a material consisting essentially of fat is at least twice, or at least four times, the reflectance of the probe beam from an interface between the optical coupler and a material consisting essentially of one of muscle, blood vessels, and skin.

The refractive index of the optical coupler can be greater than the first index. The treatment beam source can be configured to direct the treatment beam to the substrate through the optical coupler. The treatment beam produced by the treatment beam source can have a wavelength different than that of the probe beam produced by the probe beam source. The treatment beam produced by the treatment beam source can have a power greater than that of the probe beam produced by the probe beam source.

The optical coupler can be made of one of sapphire, fused silica, BK-7 glass, fint glass, germanium, and zinc selenide. Each of the probe and treatment beam sources can be a Nd:YAG laser, CTE:YAG laser, ErCr:YSGG laser, holmium laser, erbium laser, $CO_2$ laser, diode laser, or dye laser. The probe beam source can also be a light emitting diode.

In general, in another aspect, the invention features a probe for selectively delivering laser radiation to a first substrate (e.g., biological tissue) having a first index of refraction relative to a second substrate (e.g., biological tissue) having a second index of refraction less than the first index. The probe includes a laser transmitting medium including an optical axis and a substrate-contacting, e.g., tissue-contacting, surface. The optical axis contacts the tissue-contacting surface at an angle that is less than the critical angle for an interface between the tissue-contacting surface and the first tissue and greater than or equal to the critical angle for an interface between the tissue-contacting surface and the second tissue, wherein during operation the probe directs the laser radiation along the optical axis to the tissue-contacting surface.

In another aspect, the invention features an additional probe for selectively delivering laser radiation to a first tissue having a first index of refraction relative to a second tissue having a second index of refraction less than the first index. The probe includes a laser transmitting medium including an optical axis and a tissue-contacting surface, the optical axis forming an angle with the tissue-contacting surface. During operation, the probe directs the laser radiation along the optical axis to the tissue-contacting surface, transmits a first amount of laser energy through the tissue-contacting surface when contacting the first tissue, and transmits a second amount of laser energy through the tissue-contacting surface when contacting the second tissue. The angle is selected such that the first amount of laser energy is at least twice, and in some embodiments at least four times, the second amount of laser energy.

Embodiments for either of the probes described above can include any of the following features.

The angle can be substantially equal to a principle angle for optimal transmission when the tissue-contacting surface contacts the first tissue. The first tissue can consist essentially of fat and the second tissue can consist essentially of muscle, blood vessels, or skin. The first index of refraction can be greater than 1.4 at the wavelength of the laser radiation.

The probes can further include an optical fiber defining the optical axis, wherein during operation the fiber directs the laser radiation to the tissue-contacting surface. The probes can further include a prism connected to an end of the optical fiber, wherein during operation the fiber directs the laser radiation into the prism through a first face of the prism and towards a second face of the prism, the second face of the prism forming the tissue-contacting surface. In some embodiments, the laser radiation reflected from the second face of the prism can propagate along a path within the prism that is substantially normal to a third face of the prism having a reflective coating. In other embodiments, the probes can further include a second fiber, and the second and one or more additional faces of the prism direct laser radiation reflected from the second face to the second fiber, which carries the reflected radiation away from the prism.

The invention also features an apparatus that includes the probe and a laser radiation source coupled to the probe for delivering the laser radiation to the probe. The laser radiation source can include a diode laser, Nd:YAG laser, CTE:YAG laser, ErCr:YSGG laser, holmium laser, erbium laser, $CO_2$ laser, or dye laser.

In a further aspect, the invention features a method for selectively delivering laser radiation to a first tissue relative to a second tissue in which the first tissue has a first index of refraction and the second tissue has a second index of refraction that is less than the first index of refraction. The method includes contacting the first tissue in the patient with a probe; and delivering the laser radiation to the patient through the probe at a first angle of incidence greater than the critical angle for an interface between the probe and the second tissue.

The method can further include redirecting laser radiation reflected from the first tissue or second tissue in the patient back to the tissue at a second angle of incidence substantially equal to the first angle of incidence. Alternatively, the method can further include directing laser radiation reflected from the first tissue or second tissue in the patient away from the patient.

In another aspect, the invention features an additional method for selectively delivering laser radiation to a first tissue in a patient relative to a second tissue in which the first tissue has a first index of refraction and the second tissue has a second index of refraction that is less than the first index of refraction. The method includes contacting the patient with a probe; and delivering the laser radiation to the patient through the probe at an angle of incidence such that the energy transmitted into the first tissue when the probe contacts the first tissue is at least twice, and in some embodiments, at least four times, the energy transmitted into the second tissue when the probe contacts the second tissue.

Biological tissue is solid tissue from, or in, a human, animal, or plant. Fat-containing tissue is biological tissue characterized by a relatively high lipid concentration including, for example, subcutaneous fat, lipomas, liposarcomas, arteriosclerotic fat, granulomas, xanthelasmas, xanthomas, intraperitoneal fat, and retroperitoneal fat. Biological tissue that contains little or no fat includes, for example, muscle, skin, blood vessels, other organs, and cartilage. At some wavelengths, the refractive index of other tissues, e.g., bone, teeth, and calculi (stones), is greater than that of fat. When desired, embodiments of the invention can be used to selectively affect, e.g., ablate, these high-index tissues.

The critical angle $\theta_c$ for a probe/substrate interface is defined by $\theta_c = \sin^{-1}(n'/n)$, where n is the refractive index of the probe, n' is the refractive index of the substrate, and the substrate can be absorbing or non-absorbing. In the latter case, the critical angle corresponds to the angle for total internal reflection (TIR).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The inventions have many advantages. For example, the systems can selectively deliver or couple laser radiation to biological tissue. Thus, selected tissue, e.g., fat-containing tissue, can be ablated or melted, while adjacent tissue, e.g., muscle, is left unharmed. Also, the system can be used in a large number of surgical procedures, e.g., open surgery, subcutaneous procedures, endoscopic procedures, catheter procedures, and arteriosclerotic procedures. Furthermore, since there are many wavelengths at which different types of biological tissues have substantially different indices of refraction, the system can be used with many readily available laser sources that operate at such wavelengths. For example, to distinguish certain biological tissues from others, the system can be used with a holmium laser operating at a wavelength of 2.1 microns, a diode or dye laser operating in the visible to near-infrared region, a $CO_2$ laser operating in the infrared region, an Er:YSGG laser operating at a wavelength of 2.79 microns and other erbium lasers operating between wavelengths of 2.5 and 3.0 microns, thulium lasers operating at wavelengths between 1.94 to 2.01 microns, a CTE:YAG laser, and a ErCr:YSGG laser, the latter two lasers operating at wavelengths of about 2.7 microns.

There are also particular advantages to each of the passive and active aspects of the go invention. For example, in some ways the passive system is simpler because only a single beam is necessary—that beam functioning as both the probe and treatment beam. However, there are also many advantages to the active system. For example, because the probe beam is used only to distinguish one type of tissue from another, but not used to cause photophysical or photochemical change in the target area, it can be less intense than it would need to be were it to also function as the treatment beam. As a result, when the probe beam is reflected from the target area, that reflected beam is more easily dissipated, thereby improving safety.

Moreover, by having separate probe and treatment beams, their respective wavelengths (and thus the choice of laser source to provide them) can be independently optimized. In particular, the wavelength for the probe beam can be chosen to correspond to refractive indices that optimize the difference in reflection or transmission between the materials to be distinguished, without concern for whether laser radiation at that wavelength is suitable for causing any photophysical or photochemical change in at least a selected one of the materials. Conversely, the wavelength for the treatment beam can be chosen to cause the desired photophysical or photochemical change in at least a selected one of the materials, without concern for whether the refractive indices corresponding to that wavelength are suitable for distinguishing the different material that may be present in the target area.

Finally, the active control system permits the treatment beam to be selectively delivered to a first material having a first refractive index, and not a second material having a second refractive index, even when the first refractive index is less than the second refractive index.

Other features and advantages of the invention will be apparent from the following detailed description, and from the claims.

BRIEF DESCRIPTION OF THE DRAWINGS

FIG. 6 is for a fused silica probe and 2.69 micron wavelength radiation, FIG. 7 is for a sapphire probe and 2.69 micron wavelength radiation, and FIG. 8 is for a flint glass probe and 2.13 micron wavelength radiation.

DETAILED DESCRIPTION

Figure 1:
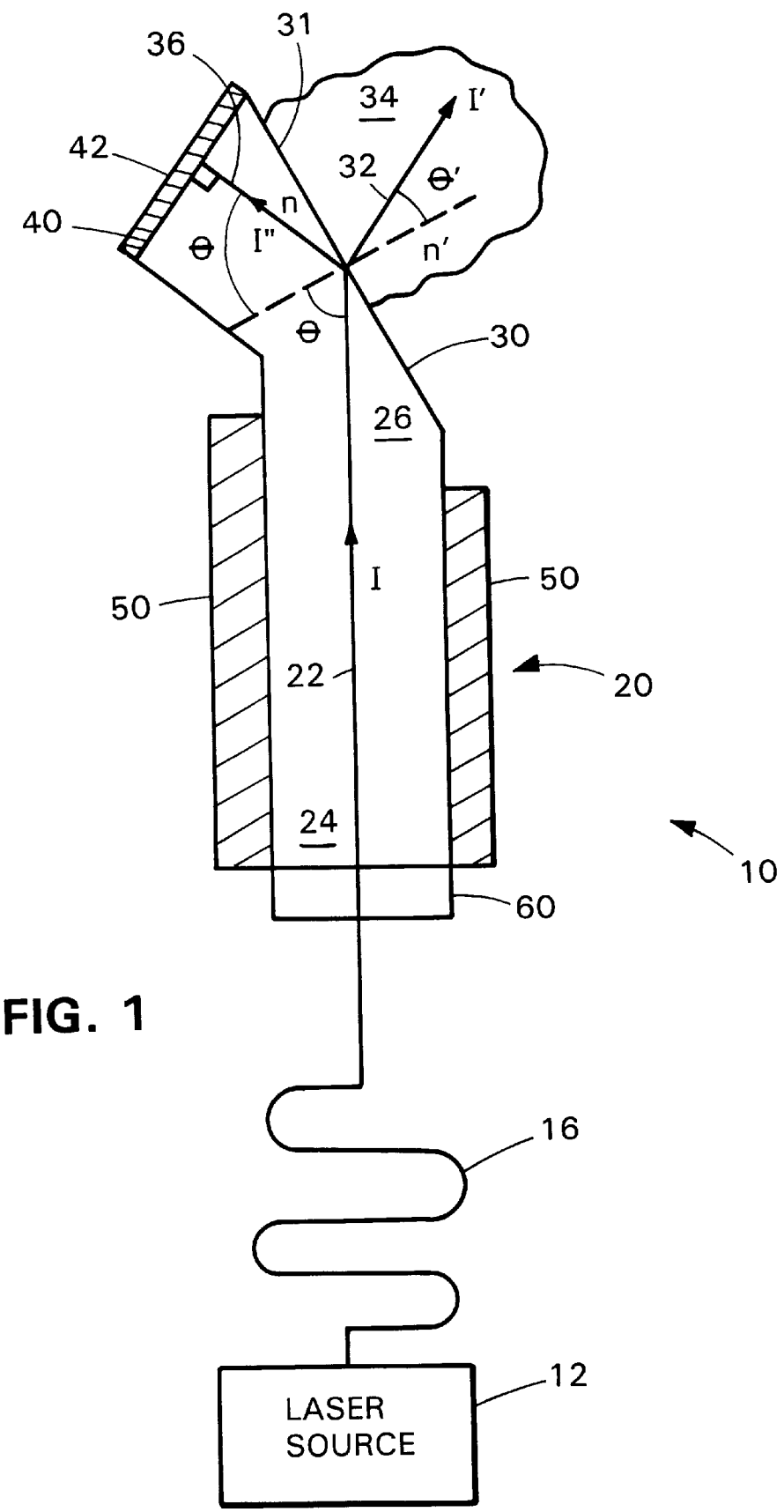
FIG. 1 is a schematic of a system for selectively delivering laser radiation to a material such as a tissue.

The invention features a surgical probe that has a surface configured to contact a material, such as biological tissue, and that carries laser radiation within the probe to the probe surface at an angle of incidence different from normal incidence. When the probe surface contacts biological tissue, the fraction of laser energy transmitted to the biological tissue from the probe will depend on the angle of incidence, the polarization of the laser radiation, the index of refraction of the probe, the index of refraction of the tissue, and the absorption of the tissue.

The probe is designed to selectively transmit a substantial portion, e.g., greater than 70%, of the laser radiation through the probe surface to the biological tissue if that tissue has an index of refraction greater than a threshold value, and to reflect a substantial portion, e.g., greater than 70%, of the laser radiation from the surface if the tissue has an index of refraction less than that threshold value. The shape and material of the probe can be varied to provide a threshold value suitable to selectively distinguish between particular types of tissues. In particular, the shape of the probe can be constructed to deliver the laser radiation to the surface at a specified angle of incidence, and the material of the probe can be selected according to its refractive index. In specific embodiments, the probe can be designed to selectively transmit laser radiation to fat-containing tissue, and not to other types of tissue such as muscle, skin, blood vessels, and organs, which have an index of refraction lower than that of fat-containing tissue.

The probe can be part of either a passive control system or an active control system. In the passive control system, the laser radiation that is selectively delivered by the probe to one type of biological tissue, and not another, is also therapeutic, in that it causes photophysical or photochemical change in the selected tissue (e.g., ablation or melting of that tissue). In the active control system, the reflectance or transmission of the laser radiation incident on the target area through the probe ("the probe beam") is monitored to determine whether or not the target area corresponds to a particular type of tissue. When the monitored reflectance or transmission of the probe beam indicates that the target area corresponds to the particular type of tissue, a second beam ("the treatment beam") is delivered to the target area. The treatment beam may be derived from the same source as that of the probe beam or a different source, the treatment beam may also be delivered to the target area through the probe. Alternatively, the treatment beam may be delivered to the target area through free space or through a separate probe. For example, the probe can be passed over multiple areas to collect data indicating which particular areas should be subject to the treatment beam, and the treatment beam can subsequently be delivered to those areas based on the collected data.

The passive control system is described first.

General Passive System

FIG. 1 shows a system 10 for selectively delivering laser radiation from a source 12 to a specific biological tissue 34. Optical fiber 16, or some other optical delivery mechanism, e.g., mirrors, waveguides, or articulated arms, guide laser radiation having wavelength λ from source 12 to the proximal end 24 of a laser radiation delivery probe 20. The probe has a shape and structure that allows the laser radiation to propagate within the probe along a path 22, which forms an angle θ with a surface 30 at the distal end 26 of probe 20. Surface 30 is substantially planar extending perpendicular to the plane of FIG. 1, and is designed to contact, and form an interface 31 with, biological tissue 34, as shown in FIG. 1.

Upon striking interface 31, the laser radiation having an irradiance I, splits into a first portion having an irradiance I', which transmits through the interface into tissue 34 along a refracted path 32 that forms an angle θ' with interface 31, and a second portion having an irradiance I", which reflects from surface 30 and propagates within probe 20 along a reflected path 36. The relative energies I'/I and I"/I depend on the indices of refraction n and n' for probe 20 and biological tissue 34, respectively, the wavelength λ, the angle of incidence θ, the polarization of the laser radiation, and the absorption at wavelength λ of biological tissue 34.

For the specific wavelength λ, the index of refraction n and angle of incidence θ defined by probe 20 are such that the transmitted energy $I_{n1'}$ when surface 30 contacts tissue 34, e.g., fat, having an index $n'=n_1'$ is substantially larger than the transmitted energy $I_{n2'}$ when the surface 30 contacts tissue 34, e.g., muscle, having an index $n'=n_2'$, where $n_1'>n_2'$. For example, in many cases $I_{n1'}/I_{n2'}$ is greater than about 2, in some cases $I_{n1'}/I_{n2'}$ is greater than about 4, and in further cases $I_{n1'}/I_{n2'}$ is greater than about 10. The selectivity of the probe is proportional to this ratio.

In some embodiments, probe 20 delivers laser radiation such that the angle of incidence θ defined when surface 30 contacts tissue 34 is less than a critical angle for tissue 34 having an index $n'=n_1'$, and greater than a critical angle for tissue 34 having an index $n'=n_2'$, wherein the critical angle $θ_c$ for tissue 34 is defined by:

$$θ_c = \sin^{-1}(n'/n) \tag{1}$$

where n is the refractive index of probe 20 and n' is the refractive index of tissue 34. In many such cases, the laser radiation is substantially reflected by the tissue having the index $n'=n_2'$ and only partially, if at all, reflected by the tissue having the index $n'=n_1'$. This is especially true for tissues that do not absorb, or only weakly absorb, the wavelength of the laser radiation. In particular, for non-absorbing tissues, the critical angle $θ_c$ is the angle at which total internal reflection (TIR) occurs for light propagating from a high-index medium (the probe) to a low-index medium (the tissue). In such cases, the laser radiation is totally reflected by the tissue having the index $n'=n_2'$.

Furthermore, since the angle of incidence is greater than the critical angle for the low index tissue, it will also be greater than the critical angle for a probe/air interface, since air has a refractive index equal to about 1. Thus, when the probe is not contacting any tissue, the laser radiation undergoes total internal reflection from the probe/air interface, thereby preventing accidental delivery of laser radiation to non-target tissue.

Mathematical Description and Probe Design

In general, the relative energy I"/I reflected by tissue 34 when contacted by surface 30 of the probe is determined by decomposing the incident laser radiation I into its parallel and perpendicular polarization components and using the Fresnel equations shown below:

$$R_\perp = \left| \frac{n\cos\theta - [(n' - ik')^2 - n^2\sin^2\theta]^{1/2}}{n\cos\theta + [(n' - ik')^2 - n^2\sin^2\theta]^{1/2}} \right|^2 \quad (2)$$

$$R_{\prime\prime} = \left| \frac{(n' - ik')^2\cos\theta - n[(n' - ik')^2 - n^2\sin^2\theta]^{1/2}}{(n' - ik')^2\cos\theta + n[(n' - ik')^2 - n^2\sin^2\theta]^{1/2}} \right|^2 \quad (3)$$

where $R_{\prime\prime}$ and $R_\perp$ are the relative reflectances for parallel and perpendicular polarizations, respectively, n' and k' are the real and imaginary parts, respectively, of the complex refractive index for tissue 34, n is the refractive index of probe 20, which is assumed to be non-absorbing, or negligibly absorbing, and $\theta$ is the angle of incidence. The incident laser radiation I may be polarized, e.g., by polarizer 60 in FIG. 1, parallel, perpendicular, or some intermediate polarization, and it may also be randomly polarized (in which case on average it has equal energies of parallel and perpendicular polarizations).

Note that the imaginary part of the refractive index, k, can be related to the absorption coefficient $\alpha$ used in the well-known Lambert's law for absorption of light irradiance I propagating through an absorbing medium along an axis x, i.e., $I(x)=I(x=0) * \exp(-\alpha x)$, by $\alpha=4\pi k/\lambda$.

Eqs. 2 and 3 above can be used to calculate the effectiveness of a probe characterized by a refractive index n and an angle of incidence $\theta$ for selectively delivering laser radiation to different types of solid, biological tissue based on their different refractive indices. In addition, these equations can be used to determine optimal parameters, n and $\theta$, to design a probe that substantially delivers laser radiation to a first type of biological tissue having a refractive index $n_1'$, e.g., fat, and not to a second type of biological tissue having a refractive index $n_2'$, e.g., muscle.

For example, in cases where absorption by the biological tissues can be ignored, i.e., k'<<n', a probe having parameters n and $\theta$ that satisfy $$n_1' > n \sin\theta > n_2' \quad (4)$$

will produce total internal reflection from the second type of tissue while delivering at least some laser radiation to the first type of tissue. Even in cases where the biological tissue is only weakly absorbing, e.g., k'/n'<0.01, the reflection from the second type of tissue for a probe satisfying Eq. 4 is typically greater than 80%.

In addition to designing the probe with an n and $\theta$ that increase, and in some cases maximize, reflection from the second type of biological tissue, the reflection from the first type of biological tissue should be decreased, and in some cases minimized. For example, for parallel polarized light there is a minimum in reflection for some intermediate angle $\theta$, known as the principle angle. In particular, if absorption is negligible, i.e., take k'=0, Eq. 4 shows that when $\theta=\tan^{-1}(n_2'/n_1')$, the reflectivity for parallel polarized light is minimized with $R_{\prime\prime}=0$.

Examples of calculations using Eqs. 2 and 3 to design the probe such that it is especially suitable for selectively delivering laser radiation to fat and not to muscle are described below. The calculations can also be extended to distinguishing other types of materials.

Probe Shapes and Materials

Probe 20 can have a variety of shapes and can be made from a variety of materials. What is important is that probe 20 receives laser radiation from source 12 and carries that laser radiation along an internal path, e.g., path 22, that intersects the tissue-contacting surface 30 with a suitable angle of incidence, $\theta$, as shown in FIG. 1. As described above, the angle $\theta$ and index n of probe 20 determine which types of tissue 34 selectively receive laser radiation from probe 20.

It is also important that laser radiation internally reflected from surface 30 does not undergo additional reflections within probe 20 that redirect the laser radiation back to surface at an angle different from the angle $\theta$. If this were the case, transmission of the redirected radiation through surface 30 could undermine the selectivity provided by the initial interaction of the laser radiation with surface 30.

To prevent laser radiation internally reflected within probe 20 from being incident on surface 30 at angles other than $\theta$, probe 20 includes an additional surface 40 that is substantially normal to the reflected laser radiation. Like surface 30, surface 40 is substantially planar, extending perpendicular to the plane of FIG. 1. Laser radiation propagates along path 22, intersects surface 30 with an angle of incidence equal to $\theta$, and that radiation reflected from surface 30 reflects from the surface with an angle equal to $\theta$. As shown in FIG. 1, the reflected radiation then propagates within probe 20 along a path 36 towards surface 40. Since surface 40 is normal to path 36, laser radiation reflected from surface 40 propagates back along path 36 towards surface 30. This retroreflected laser radiation again intersects surface 30 with an angle of incidence equal to $\theta$, and thereby delivers laser radiation to tissue 34 with the same selectivity as the first pass. Laser radiation reflected from surface 30 a second time propagates back along path 22 towards fiber 16, where it can be absorbed or reflected back to surface 30. Surface 40 can include a reflective coating 42, e.g., a thin metal film for the case of visible or infrared laser radiation, which insures that the laser radiation only exits distal end 26 of the probe through surface 30. Alternatively, in place of the reflective coating, surface 40 can include an adjacent absorber or diffuser that dissipates the laser radiation.

As shown in FIG. 1, the elongate portion of probe 20 along path 22 can be surrounded by a housing 50 that only exposes distal end 26 of the probe to tissue 34. Also, in other embodiments, the housing can surround surface 40 so that only the tissue contacting surface 30 is exposed to tissue 34. Housing 50 provides mechanical stability to probe 30, and may be used as a handle if the probe is manipulated manually by a surgeon. Alternatively, housing 50 can also provide a mechanical connection to a device, e.g., a catheter guide wire or an endoscopic medical instrument, when the probe is used internally in a patient and manipulated at a distance by a surgeon.

In various embodiments, the portion of probe 20 that provides path 22 can be shorter or longer than that shown in FIG. 1, and probe 20 can be wider or thinner than that shown in FIG. 1. The precise dimensions depend on the specific application. For example, for open surgical procedures, the diameter of tissue-contacting surface 30 may be in the range of about 2 mm to 1 cm, whereas for angioplasty applications, the diameter may on the order of about 0.5 to 3.0 mm.

Another example is endoscopic or laparoscopic surgery in which fatty tissue adherent to bowel or other delicate structure can be ablated. Bone, teeth, and calculi (e.g., kidney stones) also have higher refractive indices than adjacent fleshy tissue and can also be treated.

Figure 2:
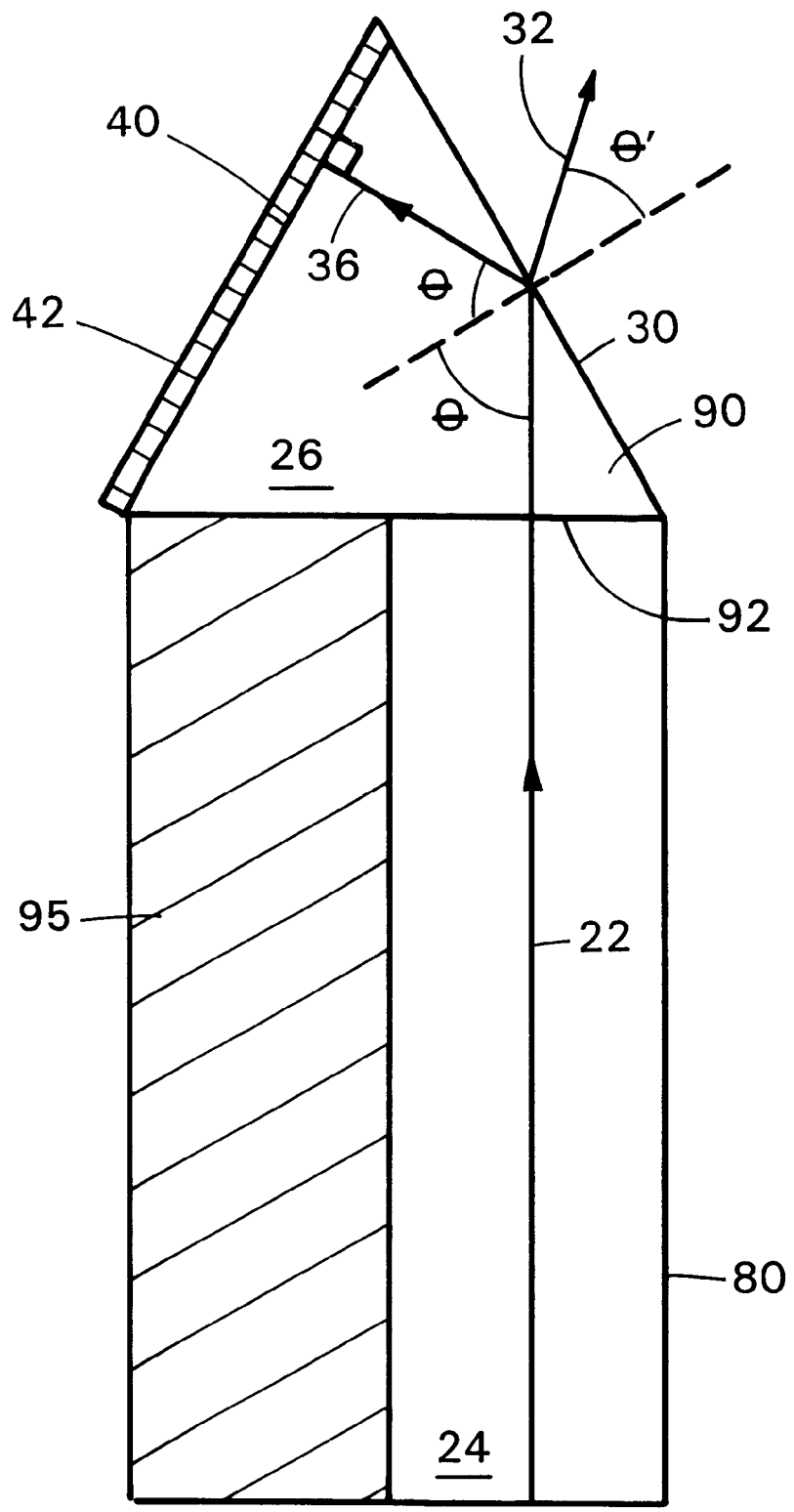
FIGS. 2, 3, 4 and 5 are schematics of different embodiments of a probe for selectively delivering laser radiation to specific tissues.

In some embodiments, probe 20 includes an optical fiber and a prism. For example, as shown in FIG. 2, an optical fiber 80 forms the distal end 24 of probe 20 and a prism 90 connected to fiber 80 forms the proximal end 26 of probe 20. The prism connects to the fiber at a surface 92 and also includes tissue-contacting surface 30 and surface 40. The laser radiation propagates within fiber 80 along path 22, which is along the length of the fiber, and into prism 90, where it intersects the tissue-contacting surface 30 at an angle of incidence $\theta$ and is selectively transmitted to the tissue along path 32. Laser radiation reflected from surface 30 propagates within prism 90 along path 36, which intersects surface 40 at normal incidence. Surface 40 retroreflects the laser radiation back along path 36.

Prism 90 and optical fiber 80 can be made of the same material or different materials as described herein. If they are made of different materials, index-matching fluid can be used where they connect to prevent reflections from surface 92. If necessary, a support block 95 connected to prism 90 and fiber 80 can be used to provide mechanical support to the prism 90. Prism 90 in FIG. 2 is an equilateral prism with angles of 60° in which case the angle of incidence $\theta$ also equals 60°.

Figure 3:
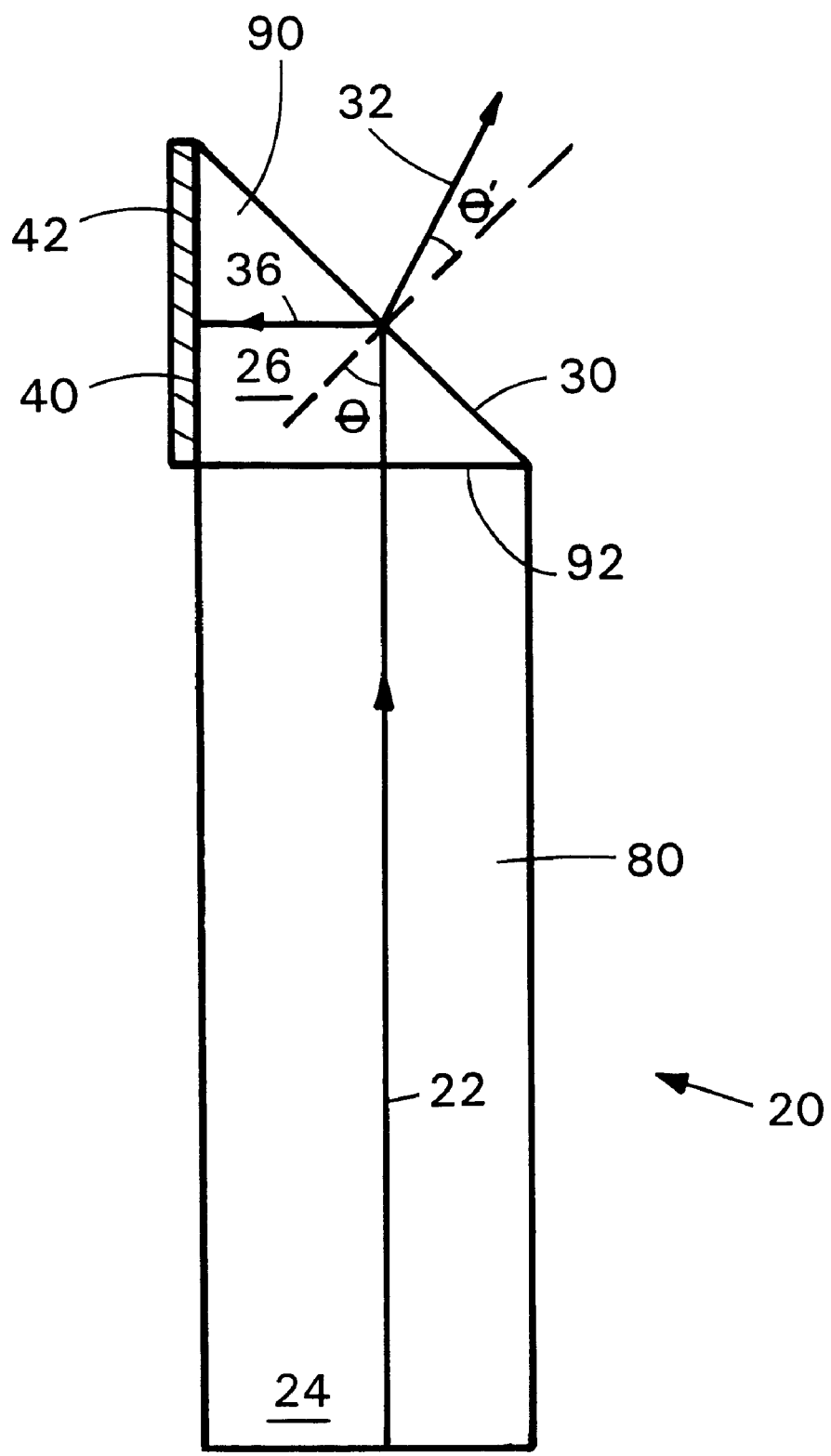

In other embodiments, prisms with different shapes and angles can also be used. For example, in FIG. 3, prism 90 is shown having angles of 45, 45, and 90 degrees and an angle of incidence $\theta$ equal to 45 degrees. As in the design shown in FIG. 2, laser radiation reflected from surface 30 propagates within prism 90 along path 36, which intersects surface 40 at normal incidence, and surface 40 retroreflects the laser radiation back along path 36. Such prisms made from, e.g., flint, BK7 glass, sapphire, or fused silica, are useful to selectively ablate fat over muscle at wavelengths between, e.g., 2 to 3 microns, as shown in the examples further below.

Figure 4:
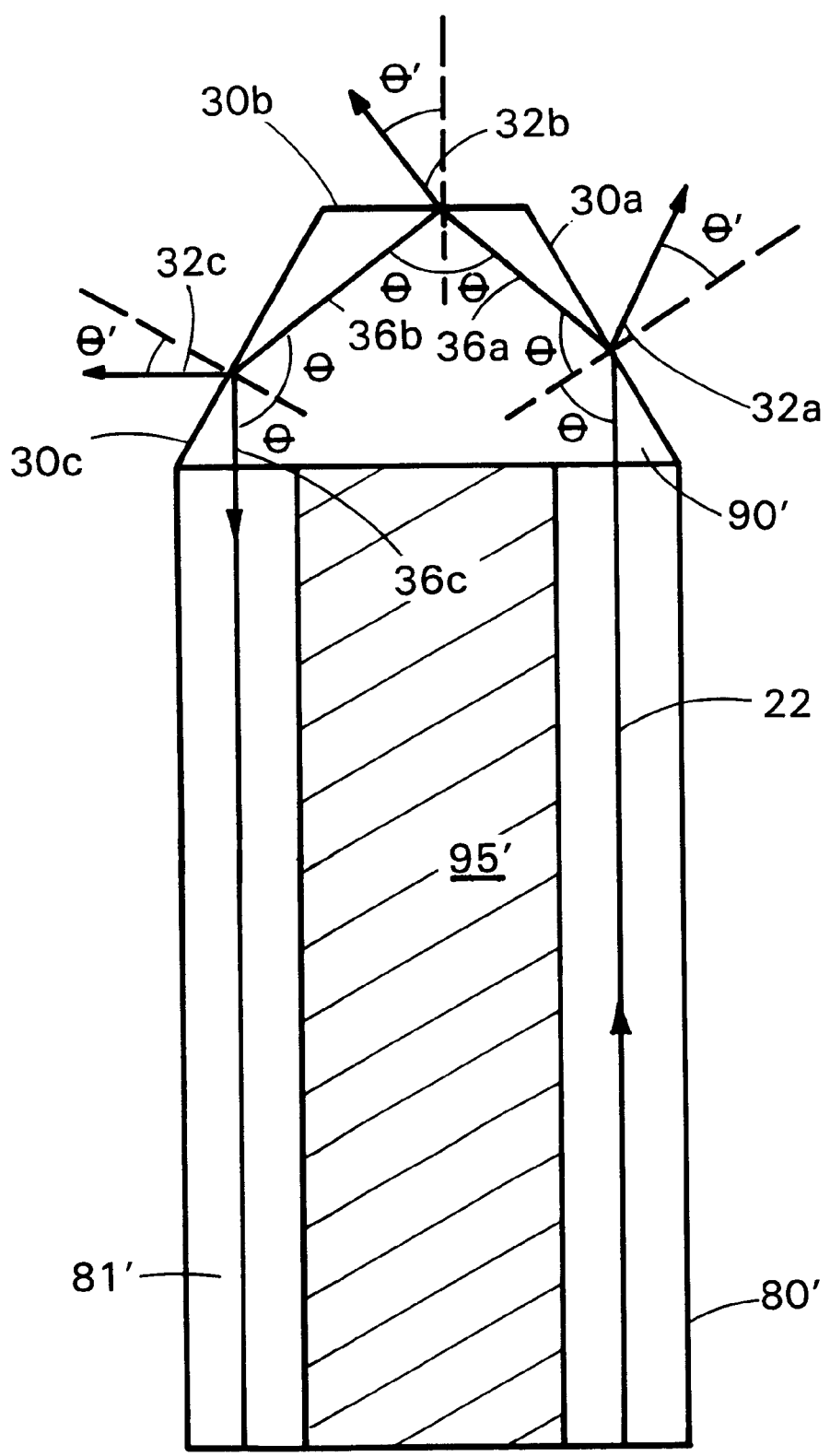

In another embodiment shown in FIG. 4, probe 20 can include a non-triangular prism 90', an input fiber 80', and an output fiber 81'. In this embodiment, prism 90' includes three surfaces 30$a$, 30$b$, and 30$c$, each of which can be used as the tissue contacting surface. Laser radiation is delivered to prism 90' along path 22 in fiber 80' and intersects surface tissue-contacting surface 30$a$ at an angle of incidence $\theta$, where it is selectively transmitted to the tissue along path 32$a$. Laser radiation reflected from surface 30$a$ propagates within prism 90' along path 36$a$, which intersects surface 30$b$ at an angle of incidence also equal to $\theta$, where it can be selectively transmitted to the tissue along path 32$b$. Laser radiation reflected from surface 30$b$ propagates within prism 90' along path 36$b$, which intersects surface 30$c$ at an angle of incidence also equal to $\theta$, where it can be selectively transmitted to the tissue along path 32$b$. Laser radiation reflected from surface 30$c$ propagates within prism 90' along path 36$c$, which directs the reflected radiation into the output fiber 81' where it is carried away from the biological tissue.

In this embodiment, prism 90' is formed such that surfaces 30$a$, 30$b$, and 30$c$ make angles of 30°, 90°, and −30° with the axis of the input and output fibers and thereby the angle of incidence $\theta$ equals 60°. Such a prism can be formed from an equilateral triangular prism that has an upper equilateral portion removed from it. A mechanical support 95' can be placed between input and output fibers 80' and 81'.

Figure 5:
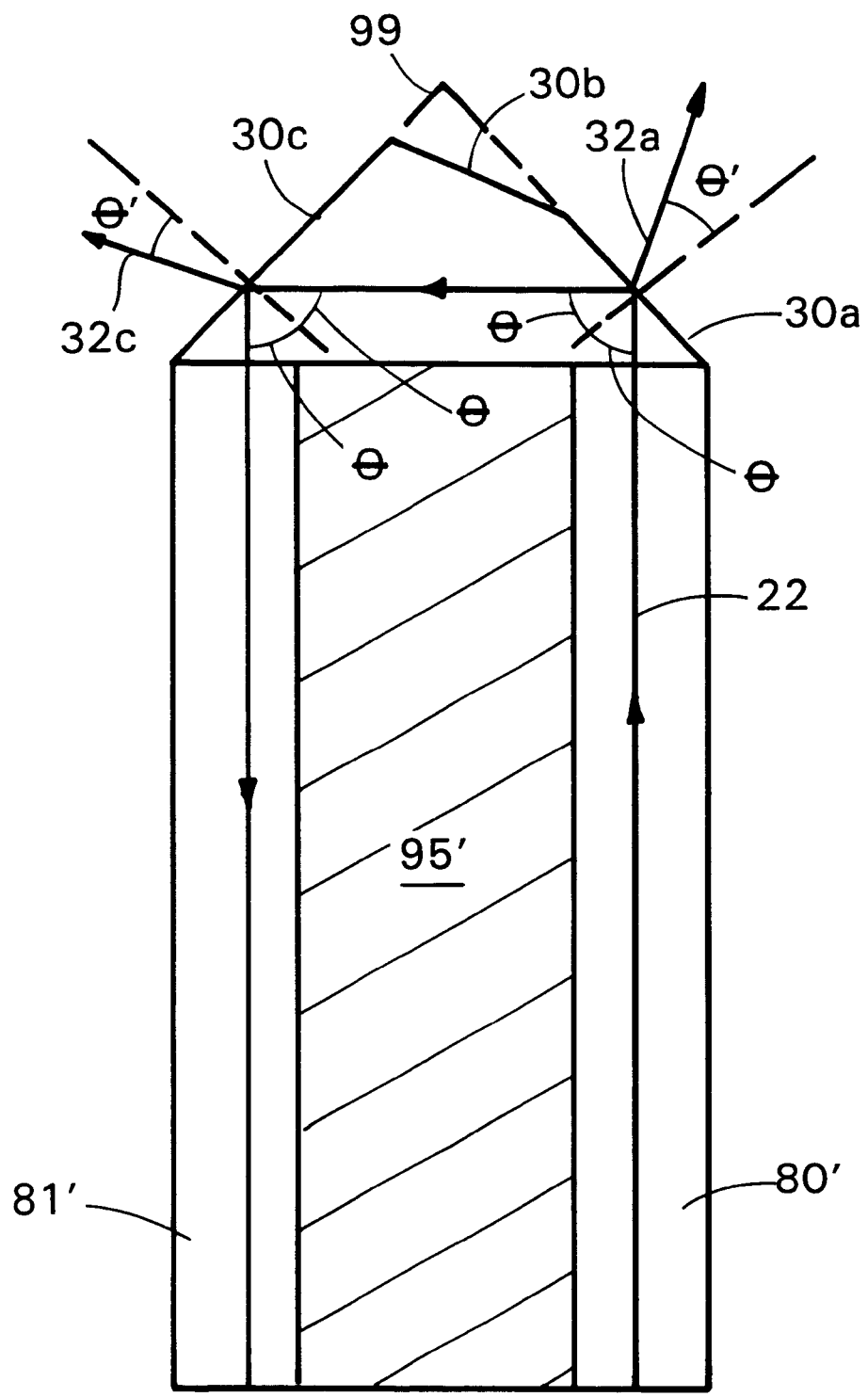

In a similar embodiment shown in FIG. 5, prism 90' is formed such that surfaces 30$a$ and 30$c$ make angles of 45° with both the axes of the input and output fibers, and the angle of incidence of the laser radiation with respect to these surfaces is also 45°. In this embodiment, the laser radiation does not intersect surface 30$b$. Such a prism can be formed from a triangular prism having angles of 45, 45, and 90 degrees in which a portion adjacent the 90° angle is removed to form surface 30$b$. Alternatively, since the laser radiation does not intersect surface 30$b$, the portion adjacent the 90° angle need not be removed, as indicated by dashed line 99 in FIG. 5.

In other embodiments, rather than attach a prism to the proximal end of a fiber, the proximal end of the fiber itself can be polished to provide the appropriate tissue contacting surface. Other embodiments are also possible, for example, the embodiments of FIGS. 4 and may have circular symmetry about an axis between the input and output fibers so that the input and output fibers are both parts of an annular waveguide that directs laser radiation to a conical prism. In such a case, the tissue-contacting surfaces are curved. Also, although not shown in FIGS. 1–5, the probes can include collimating lenses for the beams.

The prism and fiber used in the above embodiments can be made from a number of materials known in the art. For example, the fiber can be made from silica glasses, preferably those having relatively few hydroxy (OH) bonds that can lead to absorption of the laser radiation, and other materials that do not absorb the laser radiation, e.g., flint, plastics, sapphire, and liquid-filled fibers. The portion of the probe contacting the tissue at surface 30, e.g., the prism or fiber, can be made from materials including, for example, fused silica, sapphire, silicon, germanium, flint glass, BK7 glass, and zinc selenide.

Laser Sources Wavelengths and Uses

Suitable sources for the laser radiation include, for example, those lasers operating at wavelengths in the visible and infrared regions, including, e.g., diode lasers, Nd:YAG lasers, holmium lasers, erbium lasers, thulium lasers, CTE:YAG lasers, dye lasers, and $CO_2$ lasers.

Particular wavelengths that may be suitable include wavelengths in the range of about 400 to 550 nm, where dye lasers operate and where there is substantial absorption by fat, wavelengths of about 1.7 microns where some diode lasers operate and where there is also substantial absorption by fat, wavelengths of about 2.7 microns where other diode lasers operate and where the index of refraction for water is near a minimum, and wavelengths of about 10.6 microns where commercial $CO_2$ laser operate. Additional wavelengths can include 2.13 microns where commercially available Holmium:YAG lasers operate and around 2.7 microns where CTE:YAG and ErCr:YSGG lasers operate.

The precise shape, size, and material for the probe depends on the refractive and absorptive properties of the tissues to which the laser radiation is to be selectively delivered, the wavelength of that laser radiation, and the method of surgery. Referring again to FIG. 1, system 10 selectively delivers laser radiation to target tissue, and melts or vaporizes the target tissue. The wavelength of the laser radiation provided by source 12 is absorbed by, and thereby heats, the target tissue. For example, to vaporize fat-containing tissue with the laser radiation, the wavelength of the laser radiation could be within an absorption band of the fat-containing tissue. After a sufficient exposure, the laser radiation vaporizes or melts the fat-containing tissue. Alternatively, the wavelength of the laser radiation could be outside the absorption bands of the fat-containing tissue, but within the absorption bands of water contained within the fat-containing tissue. In such a case, the probe/fat interface allows the laser radiation to propagate into the fat whereupon the water contained therein absorbs the radiation and heats the fat-containing tissue until it vaporizes or melts. In contrast, a probe/muscle interface substantially prevents laser radiation from propagating into the muscle even though it is a water-rich tissue. Regardless of the mechanism, melted fat tissue can be removed from a patient through suctioning. The fluence necessary for ablation or melting can be estimated from known parameters including transmission into tissue, tissue absorption, tissue absorption coefficient, heat capacity, and pulse width.

The wavelength of the laser radiation provided by source 12 in system 10 specifies the indices of refraction of the target and adjacent tissues. For the probe to selectively deliver the laser radiation to the target tissue and not adjacent tissue, the index of refraction of the target tissue $n_1$ must be greater than the index of refraction of the adjacent tissue $n_2$. If this condition is specified, suitable values for the index of refraction n and the angle of incidence θ defined by probe 20 can be determined from Eq. 4, for the case of total internal reflection and negligible tissue absorption, or more generally from Eqs. 2 and 3. The precise index of refraction for possible probe materials and biological tissues can be determined at a number of wavelengths using optical techniques well known in the art, such as internal reflection spectroscopy, refractometry, optical retardation, and reflectance. See, for example, N. J. Harrick, Internal Reflection Spectroscopy (Harrick Scientific Corp., Ossining N.Y., 1987).

The size of probe 20 will depend on the particular application. In some embodiments, probe 20 is a hand-held device for use in open or minimally invasive surgery. In other embodiments, probe 20 connects to the end of an endoscope or a catheter placed within the patient and is manipulated by the surgeon with additional tools. For example, the probe can be inserted into blood vessels using a catheter guide wire to remove fatty deposits, e.g., arteriosclerotic fat, from therein.

The probe is particularly useful for selectively delivering laser radiation to fat-containing tissue and not to adjacent tissue such as muscle, skin, blood vessels, cartilage, and organs. The fat-containing tissue can be exposed for a period sufficient to melt and/or vaporize the fat. The melted fat can be removed by subsequent suctioning. Particular types of fat-containing tissue that can be removed by the probe include: subcutaneous fat; lipomas or liposarcomas, which are benign and malignant tumors of fat, respectively; arteriosclerotic fat, including fatty lesions prior to calcification; granulomas; xanthelasmas and xanthomas, which are fatty deposits within the skin and common within eyelids; and intraperitoneal and retroperitoneal fat, which may de removed during dissections and/or during abdominal surgery.

Active Feedback Control System

In the active control system, the reflectance of the beam delivered by the probe to one type of tissue and not another (the "probe beam") is monitored to determine what type of tissue the probe is contacting. For example, when Eq. 4 is satisfied, the probe beam substantially reflects from the probe/tissue interface when the tissue has refractive index $n_2'$, and does not substantially reflect from the interface when the tissue has refractive index $n_1'$. Thus, measurement of the reflectance indicates which type of tissue the probe is contacting. Alternatively, if the probe beam is not entirely absorbed by the tissue when transmitted through the probe/tissue interface, the intensity of the probe beam exiting the tissue can be measured to determine the transmission of the probe beam at the interface, and thereby indicate which type of tissue the probe was contacting. The measurement of the reflectance or transmission of the probe beam is the control signal for a feedback system that selectively delivers another beam, a treatment beam, to the area contacted by the probe.

Figure 9:
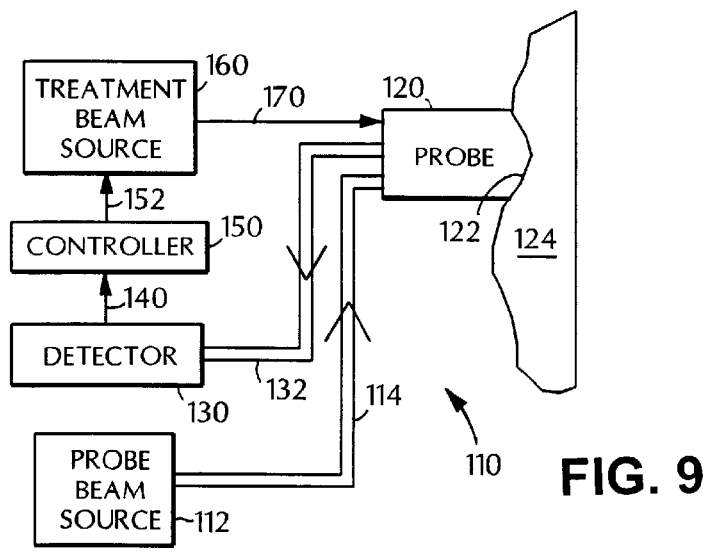
FIG. 9 is a schematic diagram of an active control system for selectively delivering laser radiation to a target area.

A schematic of the active control system 110 is shown in FIG. 9. A probe beam source 112 couples probe beam radiation into probe 120 through, e.g., free space or an input optical fiber 114. Like the probes described above, probe 120 is generally based on the equations described above, e.g., Eq. 4, and selectively delivers a probe beam into a certain type of material but not other(s). Probe 120 has a surface 122 configured to contact a target area 124, e.g., biological tissue, and the probe 120 directs the probe beam within it to be incident on surface 122 at an angle θ. The reflection of the probe beam from the probe/target interface varies with the refractive index of the target. As described above, the incident angle θ and refractive index for the probe can be selected to cause substantial reflection (e.g., greater than about 70%, 80%, or 95%) for some materials and not substantial reflection for other materials.

Unlike the probes described above, probe 120 directs the portion of the probe beam reflected from the interface to a detector 130, e.g., through an output fiber 132, and the detector measures the intensity of the reflected probe beam. Nonetheless, the previously described probes can be modified to be suitable for the active control system. For example, probe 120 can be similar to the embodiment shown in FIG. 4, which uses prism 90' and delivers probe beam radiation into prism 90' through fiber 80' and sends the reflected probe beam radiation out of the fiber through fiber 81'. In this example, to simplify the measurement at detector 130, surfaces 30*b* and 30*c* of prism 90' can be coated to be reflective, so that transmission to the target area only occurs through surface 30*a*. In other examples, probe 120 can be like the probes of FIGS. 2 and 3, except that the reflective surface 42 is replaced with output optical fiber 132 to deliver the reflected probe beam 36 to detector 130. In other embodiments, the detector can be integrated with the probe. For example, with the probes of FIGS. 2 and 3, the detector may be positioned directly at surface 40 to measure the intensity of the reflected probe beam. Furthermore, in some embodiments, the probe beam source may be integrated with the probe. In general, the detector can be any type of photodetector responsive to the probe beam radiation. For example, the photodetector can be a silicon photodiode, which is suitable for visible wavelengths such as those produced by a Helium Neon laser, or it can be an Indium Arsenide detector, which is suitable for infrared wavelengths such as those produced by a Holmium laser.

Detector 130 sends a signal 140 indicative of the reflection of the probe beam from surface 122 to a controller 150. If signal 140 indicates that the reflection of the probe beam from the surface 122 is less than a threshold amount, controller 150 sends a signal 152 to cause a treatment beam source 160 to deliver a treatment beam 170 to target area 124, e.g., through probe 120. The threshold amount can be preset by a user according to the specific application and the materials to be distinguished. For example, the threshold setting can be determined empirically by using known materials for the target area, and/or the threshold setting can be determined theoretically using Eqs. 2 and 3 and also taking into account coupling losses between the fibers and the probe. In other embodiments, controller 150 can employ multiple threshold settings that correspond to multiple power levels for the treatment beam. For example, the multiple thresholds can be used to distinguish between more than two types of materials in the target area. The controller can be an electronic device such as a circuit, an integrated circuit, or a computer. To cause the treatment beam source to deliver the treatment beam, controller 150 may control a shutter in the treatment beam source (e.g., a mechanical shutter or Pockel's cell shutter) or may control the power supply of the treatment beam source.

An important difference between the active and passive systems is that in the active system the wavelength selected for the probe beam need not be one that causes photophysical or photochemical change in the desired target tissue. Thus, the wavelength of the probe beam can be selected to optimize its selectivity, without concern for whether it causes the desired effect of the treatment beam. For example, on one hand, high absorption by the tissues to be distinguished tends to decrease selective transmission as a function of incident angle, but on the other hand, high absorption is desirable if one the tissues is to be ablated (e.g., fat). The absence of this constraint permits a greater range of choices for the probe beam radiation. Furthermore, it is not necessary for the probe beam source to produce an intense beam, because the treatment beam, not the probe beam causes the change in the target area in the active system. In the active system, suitable sources for the probe beam include, e.g., a helium neon laser, a diode laser, or collimated light from a light emitting diode (LED). The treatment beam source, on the other hand, is selected to be at a wavelength that causes photophysical or photochemical change in the desired target tissue, e.g., by being at a wavelength that is highly absorbed by the desired target material. Suitable sources for the treatment beam include a Nd:YAG laser, a CTE:YAG laser, a ErCrYSGG laser, a holmium laser, an erbium laser, other diode lasers, a dye laser, and a $CO_2$ laser.

Treatment beam source 160 can deliver the treatment beam 170 to probe 120 either through free space, or an optical fiber (not shown). Once coupled into probe 120, the treatment beam can propagate to the target area 124 along either a path common to, or different from, the probe beam. For example, if probe 120 is similar to the embodiments shown in FIGS. 2–5, the treatment beam can travel along the same path as the probe beam to reach the target area. In such embodiments, a shutter or filter can be placed adjacent the detector to prevent reflected portions of the treatment beam from overloading the detector. For example, a dichroic filter can be used to permit light at the wavelength of the probe beam from reaching the detector, but not light at the wavelength of the treatment beam. In another example, the controller can cause a shutter to close an aperture to the detector when the treatment beam is delivered to the probe.

Figure 10A:
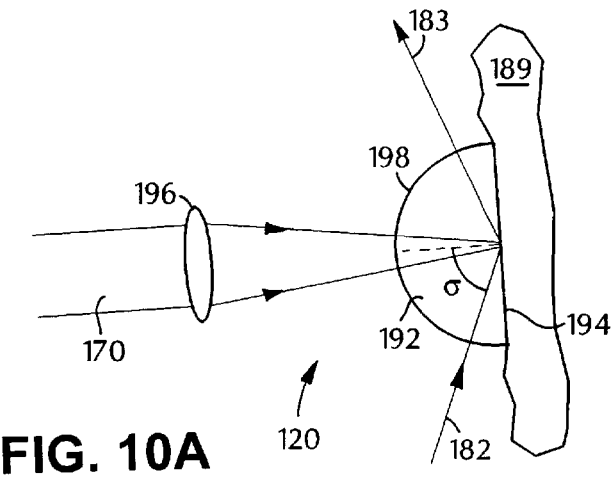
FIGS. 10a and 10b are schematic diagrams of an embodiment of a probe for use with the active control system of FIG. 9.
Figure 10B:
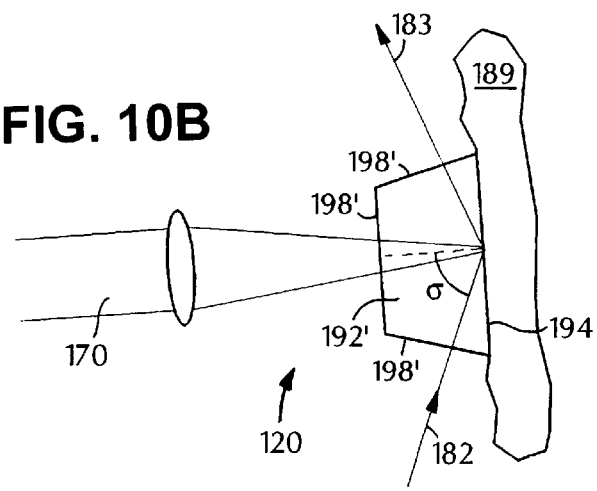

Alternatively, the treatment beam can travel along a different path than that of the probe beam as shown in the embodiment of FIGS. 10a and 10b. Referring to FIG. 10a, probe 120 includes a semicircular prism 192 having surface 194 contacting tissue 189. Prism 192 directs treatment beam 170 through it to contact surface 194 at, e.g., normal incidence, where transmission is typically highest. Probe 120 can also include a lens 196 prior to prism 192 to focus the treatment beam on surface 194, e.g., in conjunction with the curvature of the prism entry face 198. The probe beam 182 is directed into prism 192 closer to an end of the semicircular face 198, and prism 182 in turn directs probe beam 182 to contact surface 194 at the incident angle θ. The reflected probe beam 183, if any, exits prism 192 at an opposite end of the semicircular face to be measured by the detector (not shown). The semicircular profile of face 198 provides substantially normal interfaces for the treatment beam, the probe beam, and the reflected probe beam, thereby minimizing coupling losses to the prism.

Alternatively, rather than being curved, the prism can have multiple faces 198' for coupling of the probe and treatment beams into the prism, as depicted by prism 192' in FIG. 10b. Other designs for the prism are also possible. For example, the prism and lens can be integrated into a single component. Moreover, the lens may not be necessary, if the prism itself sufficiently focuses the treatment beam onto the target area. Furthermore, although not shown in FIGS. 10a and 10b, probe 120 can further include a handle, optical fibers coupling the probe and treatment beams into the prism and the reflected probe beam away from prism, and appropriate mounts for the different components.

Figure 13:
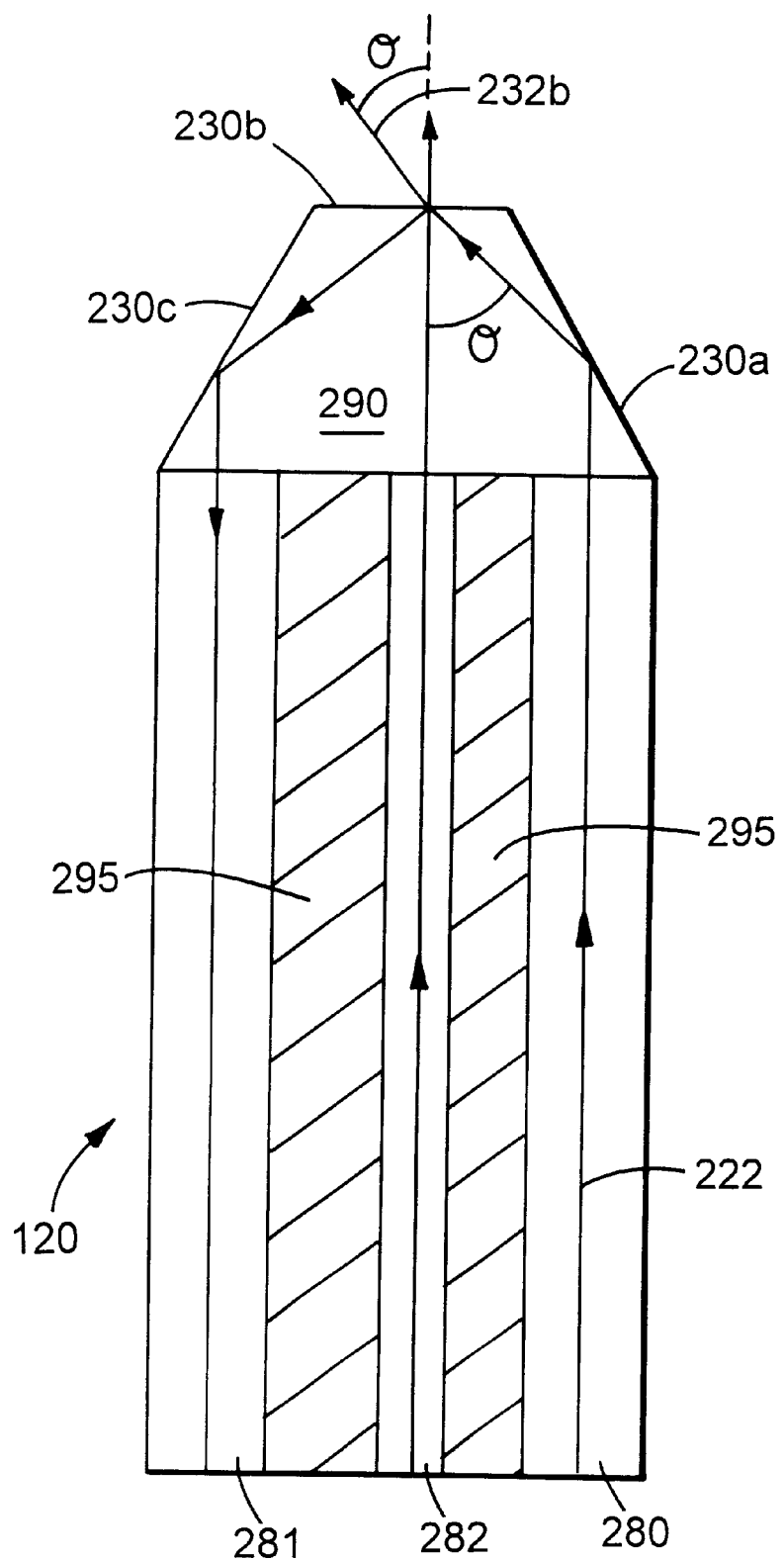
FIG. 13 is a schematic diagram of another embodiment of a probe for use with the active control system of FIG. 9.

For example, referring to FIG. 13, another embodiment for probe 120 includes a prism 290, an input fiber 280 and an output fiber 281 for a probe beam 222, and a fiber 282 for a treatment beam 170. A handle structure 295 integrates prism 290 and fibers 280, 281, and 282. Prism 290 includes three surfaces 230a, 230b, and 230c, surfaces 230a and 230c being coated to be highly reflective, and surface 230b forming the tissue-contacting surface. Probe beam 222 is delivered along fiber 280 and reflects from surface 230a to impinge on surface 230b at an angle of incidence θ, where it may be transmitted to the tissue along path 232b. Laser radiation reflected from surface 230a reflects from surface 230c and then propagates away from prism 230 along fiber 281, which delivers the reflected radiation to the detector. Based on the intensity of the reflected light recorded by the detector, the controller causes the treatment beam source to deliver treatment beam 170 to prism 290 through fiber 282, where upon it is incident on surface 230b at normal incidence and substantially transmits into the tissue contacted by surface 230b. Although not shown in FIG. 13, focusing elements can be incorporated with fiber 282 for increasing the intensity of the treatment beam at surface 230b.

EXAMPLES

The invention is illustrated by the following simulated examples, which do not limit the claimed invention.

Example 1

In this example, the reflectance from muscle and fat tissues were calculated as a function of incident angle based on Eqs. 2 and 3 for the case of 2.69 micron wavelength radiation produced by a CTE:YAG laser and delivered to the tissue through a fused silica prism. The following parameters for refractive index n and absorption k at 2.69 microns were used: $n_1$ (fat)=1.42; $n_2$ (muscle)=1.185; $k_1=k_2=0.0145$; and n (fused silica)=1.436. The laser radiation was taken as perpendicularly polarized. The relative reflectance for fat (dashed line) and muscle (solid line) are shown in FIG. 6.

Figure 6:
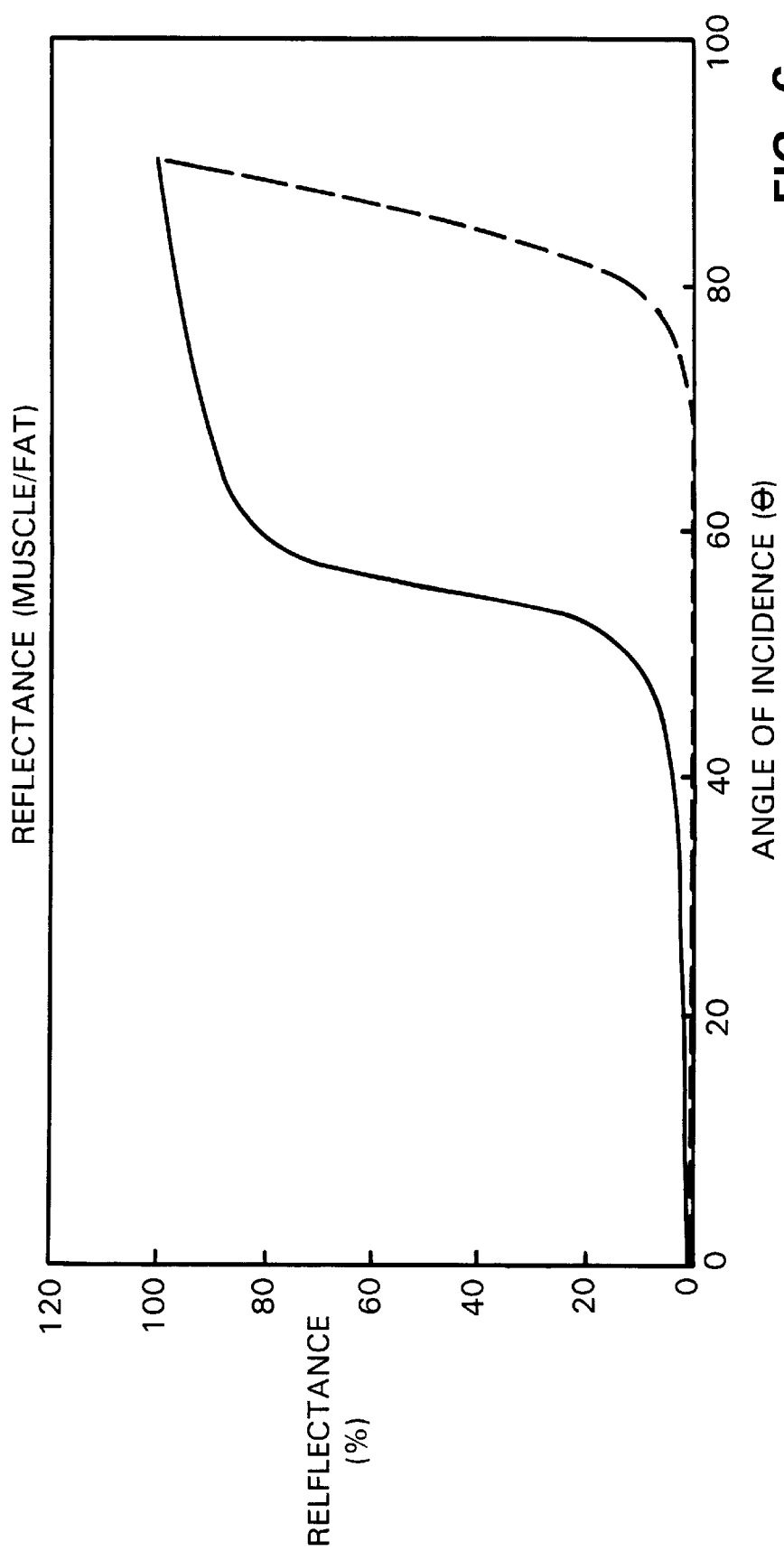
FIGS. 6, 7, and 8 are graphs showing percent reflectance from a tissue/probe interface as a function of incident angle for muscle tissue (solid line) and fat tissue (dashed line).

As shown in FIG. 6 there is substantial selectivity for incident angles between about 55° and 80°. In particular, at an incident angle of 60°, the reflectivity from muscle tissue is about 82%, whereas the reflectivity from fat tissue is about 0.1%. Thus, a probe similar to that of FIGS. 2 or 4 (those that have an incident angle of 60°) having a fused silica prism and a 2.69 micron source from a CTE:YAG laser will be suitable to selectively deliver laser radiation to fat and not muscle. The selectively delivered radiation can itself be used to heat or ablate the fat. Alternatively, measurement of the intensity of the reflected laser radiation can be used to cause delivery of an intense treatment beam to heat or ablate the fat when the reflected intensity indicates that the probe is contacting fat.

Example 2

In this example, the reflectance from muscle and fat tissue were calculated as a function of incident angle based on Eqs.

2 and 3 for the case of 2.69 micron wavelength radiation produced by a CTE:YAG laser and delivered to the tissue through a sapphire prism. The following parameters for refractive index n and absorption k at 2.69 microns were used: n1 (fat)=1.42; n2 (muscle)=1.185; $k_1=k_2=0.0145$; and n (sapphire)=1.738. The laser radiation was taken as perpendicularly polarized. The relative reflectance for fat (dashed line) and muscle (solid line) are shown in FIG. 7.

Figure 7:
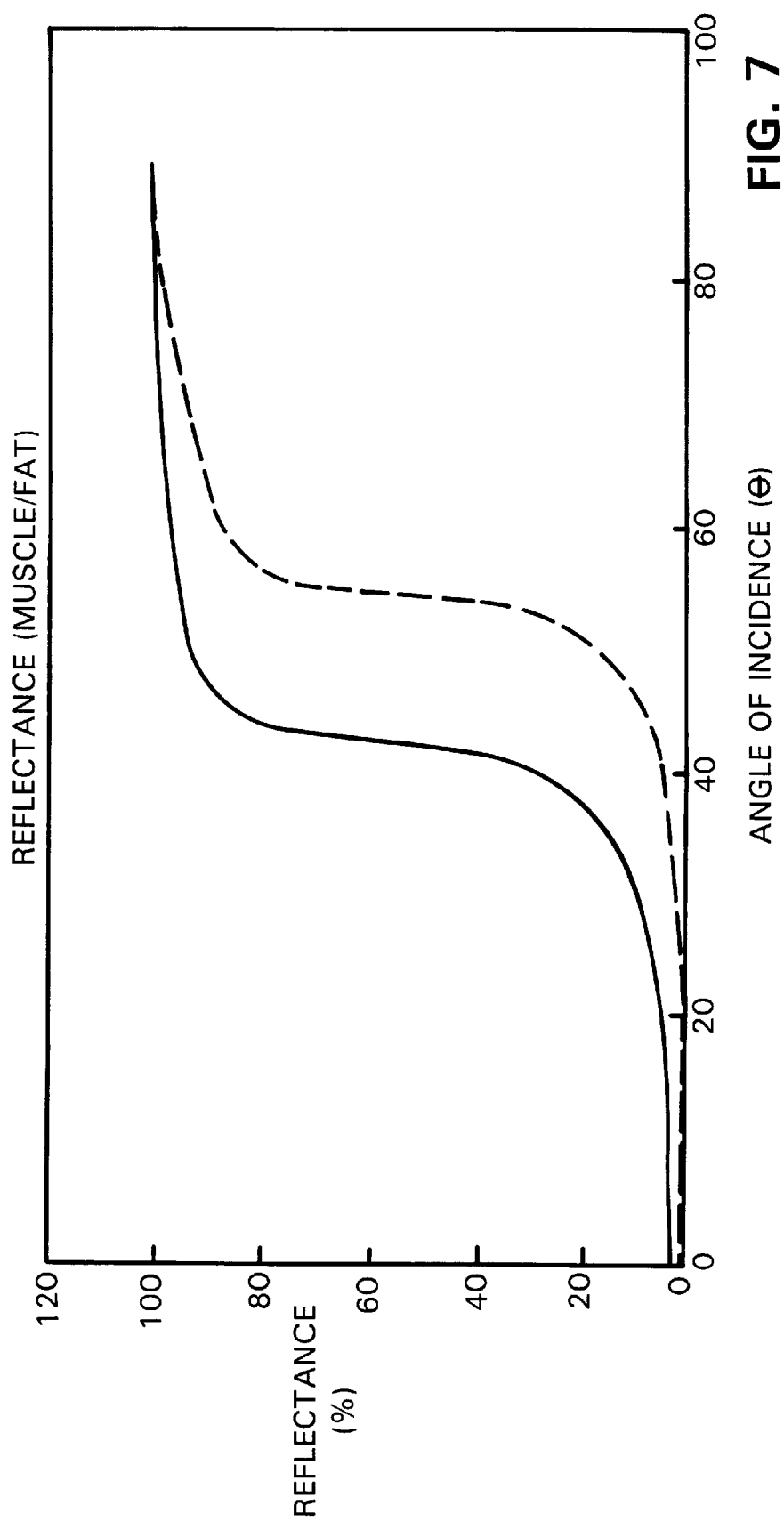

As shown in FIG. 7 there is substantial selectivity for incident angles between about 40° and 50°. In particular, at an incident angle of 45°, the reflectivity from muscle tissue is about 86%, whereas the reflectivity from fat tissue is about 7%. Thus, a probe similar to that of FIGS. 3 or 5 (those that have an incident angle of 45°) having a sapphire prism and a 2.69 micron source from a CTE:YAG laser will be suitable to selectively deliver laser radiation to fat and not muscle. Again, the selectively delivered radiation can itself be used to heat or ablate the fat. Alternatively, measurement of the intensity of the reflected laser radiation can be used to cause delivery of an intense treatment beam to heat or ablate the fat when the reflected intensity indicates that the probe is contacting fat.

Example 3

In this example, the reflectance from muscle and fat tissue were calculated as a function of incident angle based on Eqs. 2 and 3 for the case of 2.13 micron wavelength radiation produced by a Holmium:YAG laser and delivered to the tissue through a flint glass prism. The following parameters for refractive index n and absorption k at 2.13 microns were used: n1 (fat)=1.42; n2 (muscle)=1.296; $k_2=k_2=0.0004$; and n (flint)=1.588. The laser radiation was taken as perpendicularly polarized. The relative reflectance for fat (dashed line) and muscle (solid line) are shown in FIG. 8.

Figure 8:
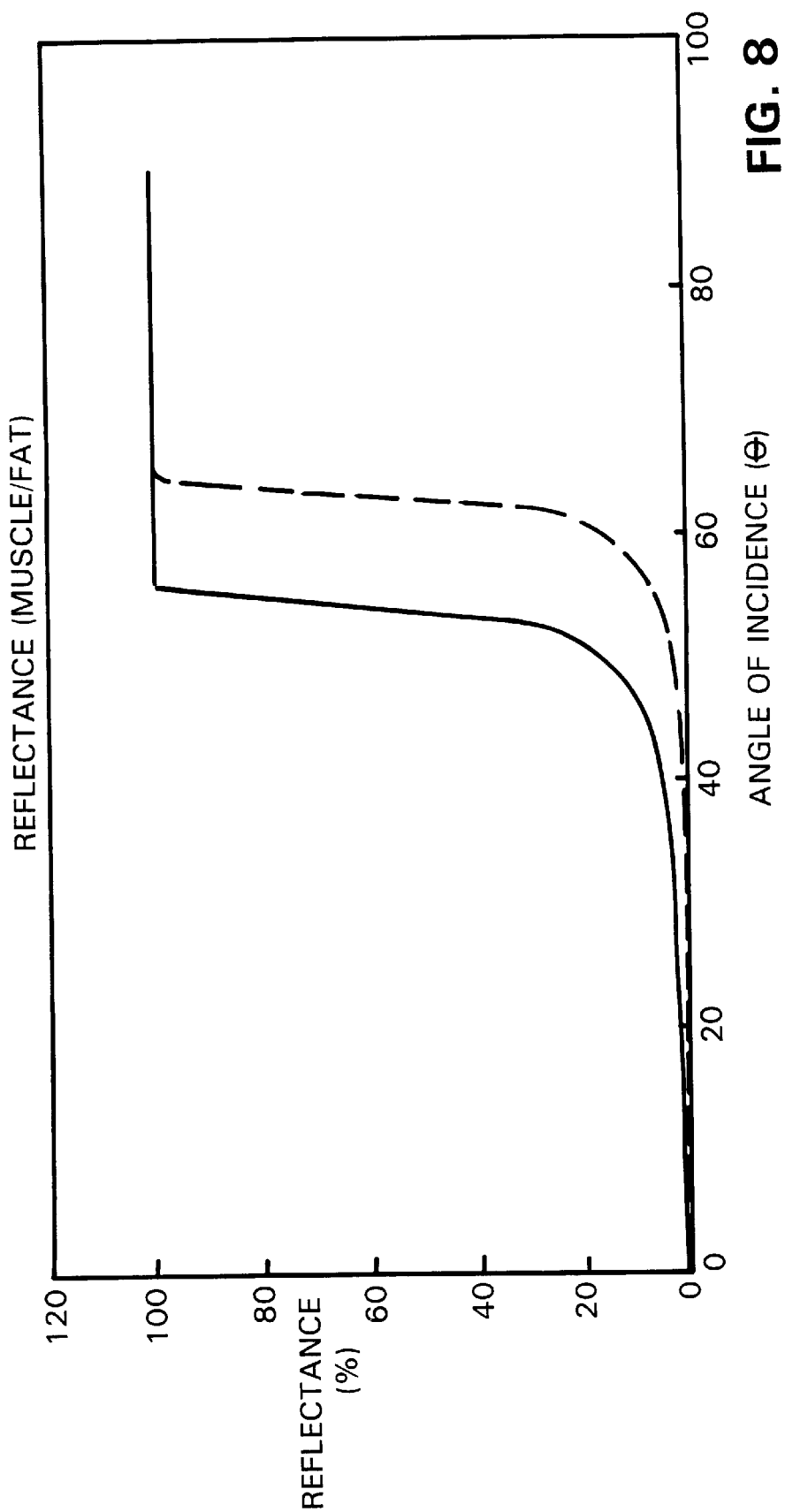

As shown in FIG. 8 there is substantial selectivity for incident angles between about 50° and 60°. In particular, at an incident angle of 56°, the reflectivity from muscle tissue is about 99%, whereas the reflectivity from fat tissue is about 6%. Thus, a probe providing an incident angle of about 55° and having a flint glass prism and a 2.13 micron wavelength delivered from a Holmium:YAG laser will be suitable to selectively deliver laser radiation to fat and not muscle. Again, the selectively delivered radiation can itself be used to heat or ablate the fat. Alternatively, measurement of the intensity of the reflected laser radiation can be used to cause delivery of an intense treatment beam to heat or ablate the fat when the reflected intensity indicates that the probe is contacting fat.

Example 4

Figure 11:
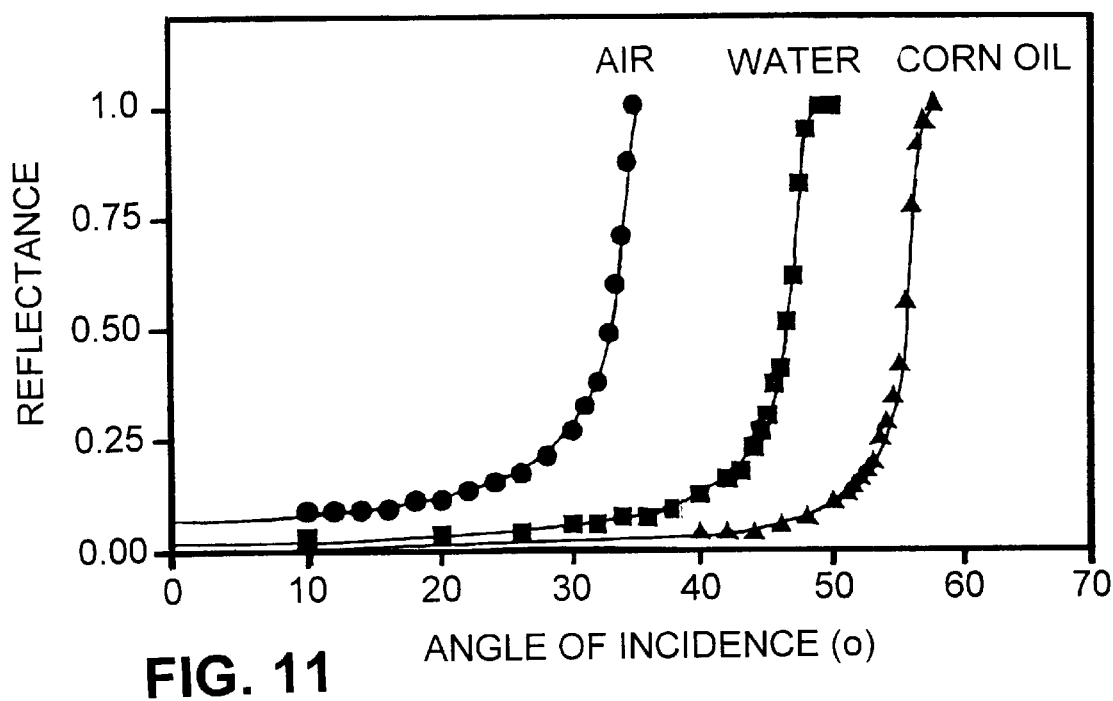
FIG. 11 is a graph showing percent reflectance from a material/probe interface as a function of incident angle where the material is air (circles), water (squares), and corn oil (triangles), and the none of the material strongly absorb the incident radiation.

This example illustrates the effect of absorption on the selective reflectance as a function of incident angle from a high index material to a low index material. FIG. 11 shows the reflectance from air (circles), water (squares), and corn oil (triangles) calculated as a function of incident angle based on Eqs. 2 and 3 for the case of 2.09 micron wavelength radiation produced by a Holmium:YAG laser and delivered to the tissue through a sapphire prism. The following parameters for refractive index n and absorption k at 2.09 microns were used: n1 (corn oil)=1.45; n2 (water)=1.292; $k_1$ (corn oil)=0.000043 cm$^{-1}$; $k_2$ (water)=0.00049 cm$^{-1}$; and n (sapphire)=1.736. The laser radiation was taken as perpendicularly polarized. As shown in FIG. 11 there is substantial selectivity for incident angles between about 45° and 55° to distinguish between corn oil and water (or air).

Figure 12:
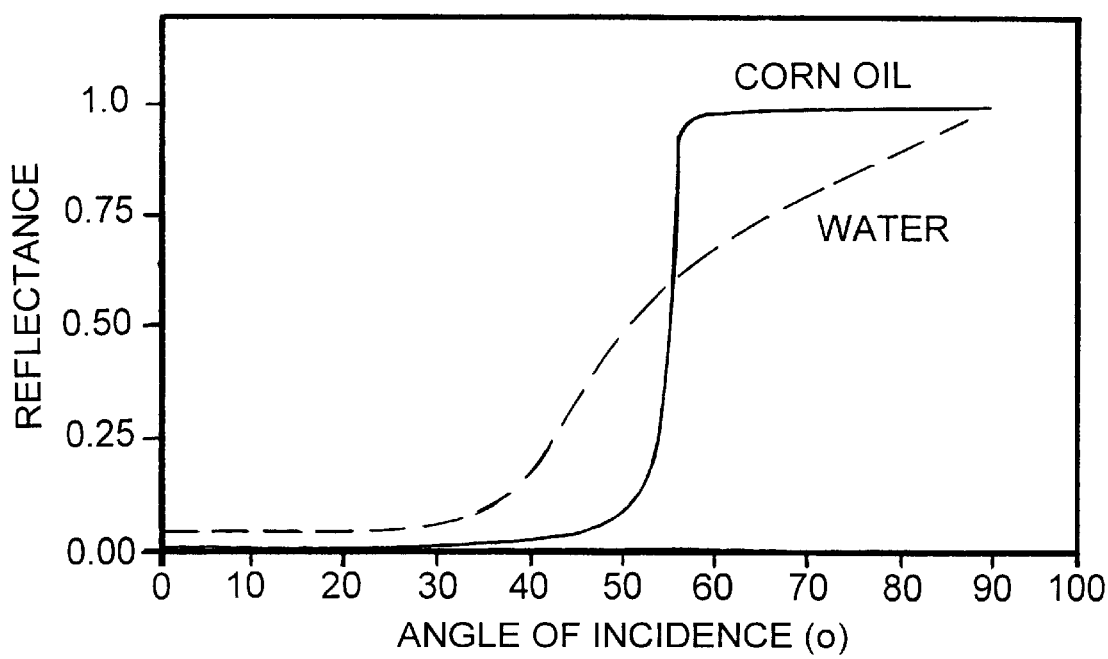
FIG. 12 is a graph showing percent reflectance from a material/probe interface as a function of incident angle where the material is water (dashed line) and corn oil (straight line), where the water strongly absorbs the incident radiation.

FIG. 12 also shows reflectance data for water and corn oil based on Eqns. 2 and 3 using a sapphire probe, but in this case, using probe radiation at 2.79 microns as produced by a Er:YSSG laser. The following parameters for refractive index n and absorption k at 2.79 microns were used: n1 (corn oil)=1.45; n2 (water)=1.091; $k_1$ (corn oil)=0.0047 cm$^{-1}$; $k_2$ (water)=0.14 cm$^{-1}$; and n (sapphire)=1.78. Thus, the absorption for water at 2.79 microns is relatively large. As a result, the data in FIG. 12 shows that the selective reflectance is more limited. Thus, probe radiation at 2.79 microns may be a poor choice to distinguish corn oil from water, even if it were the desired wavelength for treatment.

However, because the active feedback system can use separate wavelengths for the probe and treatment beams, radiation at, e.g., 2.79 microns, can be delivered to tissue as a treatment beam, without affecting the selectivity of the probe beam, which can be at, e.g., 2.09 microns, as illustrated by the present comparison.

Other Embodiments

It is to be understood that while the invention has been described in conjunction with the detailed description thereof, that the foregoing description is intended to illustrate and not limit the scope of the invention, which is defined by the scope of the appended claims. For example, in other embodiments the probe can selectively deliver laser radiation to a first non-biological substrate having a first index of refraction and not to a second non-biological substrate having a second index of refraction less than the first index. The non-biological substrates can be, e.g., metals, ceramics, plastics, semiconductors, or other solid materials. Furthermore, with regard to the active control system, in other embodiments the probe and treatment beam sources may be the same. For example, the control system can control the power of the probe beam based on its measured reflection from the probe/tissue interface, and increase the power of the probe beam so that it provides a treatment beam when the measured reflectance indicates that the desired tissue is being contacted by the probe. In such cases, the detector may include a shutter or filter to prevent damage by small amounts of the treatment beam nonetheless being reflected by the desired tissue. Also, in further embodiments, the probe can be used to scan over a range of target areas to determine which regions of the scanned area correspond to material that is to be subject to the treatment beam. The treatment beam can subsequently be directed to only such areas, in which case it need not pass through the probe used to direct the probe beam. Other aspects, advantages, and modifications are within the scope of the following claims.

What is claimed is:

1. A method for selectively delivering a treatment beam to portions of a substrate having a first index of refraction and not to other portions of the substrate having a second index of refraction less than the first index, the method comprising:

contacting the substrate with an optical coupler that delivers a probe beam to the substrate at an incident angle that is less than the critical angle for an interface between the optical coupler and a material having the first index of refraction and greater than the critical angle for an interface between the optical coupler and a material having the second index of refraction; and selectively delivering the treatment beam to the substrate based on reflectance of the probe beam from the substrate or transmission of the probe beam through the substrate.

2. The method of claim 1, wherein the treatment beam has a wavelength different than that of the probe beam.

3. The method of claim 1, where the substrate absorbs more strongly at the wavelength of the treatment beam than at the wavelength of the probe beam.

4. The method of claim 1, wherein the treatment beam is delivered to the substrate through the optical coupler.

5. The method of claim 1, wherein the treatment beam is selectively delivered to the substrate based on the reflectance of the probe beam from the substrate.

6. The method of claim 5, wherein the treatment beam is delivered to the substrate when the reflectance is less than about 0.9.

7. The method of claim 5, wherein the treatment beam is delivered to the substrate when the reflectance is less than about 0.7.

8. The method of claim 1, wherein the treatment beam has a power greater than that of the probe beam.

9. The method of claim 1, wherein the substrate is biological tissue.

10. The method of claim 9, wherein the portions of the substrate having the first index comprise fat.

11. The method of claim 10, wherein the portions of the substrate having the first index consist essentially of fat.

12. The method of claim 9, wherein the portions of the substrate having the second index comprise one or more of muscle, blood vessels, and skin.

13. The method of claim 12, wherein the portions of the substrate having the second index consist essentially of one of muscle, blood vessels, and skin.

14. The method of claim 1, wherein the portions of the substrate having the first index comprise fat and the portions of the substrate having the second index comprise one or more of muscle, blood vessels, and skin.

15. The method of claim 1, wherein the power of the treatment beam is sufficient to melt or ablate the portions of the substrate having the first index.

16. The method of claim 1, wherein the optical coupler is made from one of sapphire, fused silica, BK-7 glass, flint glass, germanium, and zinc selenide.

17. The method of claim 1, wherein the treatment beam is delivered to the substrate at normal incidence.

18. The method of claim 1, wherein the probe beam is derived from a diode laser, a helium neon laser, or a light emitting diode.

19. The method of claim 1, wherein the treatment beam is derived from a Nd:YAG laser, CTE:YAG laser, ErCr:YSGG laser, holmium laser, erbium laser, $CO_2$ laser, diode laser, or dye laser.

20. A method for selectively delivering a treatment beam to portions of a substrate having a first index of refraction and not to other portions of the substrate having a second index of refraction less than the first index, the method comprising:
   providing an optical coupler having an index of refraction greater than the second index of refraction;
   contacting the substrate with the optical coupler to deliver a probe beam from the optical coupler to the substrate at an incident angle; and
   selectively delivering the treatment beam to the region based on the reflectance of the probe beam from the substrate or the transmission of the probe beam through the substrate.

21. The method of claim 20, wherein the optical coupler has an index of refraction greater than the first index of refraction.

22. The method of claim 20, wherein the treatment beam is selectively delivered to the substrate based on the reflectance of the probe beam from the substrate.

23. The method of claim 20, wherein the incident angle is selected such that when the probe beam is incident on the substrate at the incident angle, the reflectance of the probe beam from an interface between the optical coupler and the portions of the substrate having the first index is at least twice the reflectance of the probe beam from an interface between the optical coupler and the portions of the substrate having the second index.

24. The method of claim 20, wherein the incident angle is selected such that when the probe beam is incident on the substrate at the incident angle, the reflectance of the probe beam from an interface between the optical coupler and the portions of the substrate having the first index is at least four times the reflectance of the probe beam from an interface between the optical coupler and the portions of the substrate having the second index.

25. The method of claim 20, wherein the incident angle is greater than about 10°.

26. The method of claim 20, wherein the incident angle is greater than about 30°.

27. A system for selectively delivering a treatment beam to portions of a substrate having a first index of refraction and not to other portions of the substrate having a second index of refraction less than the first index, the system comprising:
   an optical coupler having a surface configured to contact the substrate and a refractive index greater than the second index;
   a probe beam source configured to direct a probe beam into the optical coupler to contact the surface at an incident angle;
   a detector configured to measure the reflectance of the probe beam from the surface or the transmission of the probe beam through the surface;
   a treatment beam source for the treatment beam; and
   a controller which during operation causes the treatment beam source to selectively deliver the treatment beam to the substrate based on the reflectance or transmission measured by the detector.

28. The system of claim 27, wherein the incident angle is less than the critical angle for an interface between the optical coupler and a material having the first index of refraction and greater than the critical angle for an interface between the optical coupler and a material having the second index of refraction.

29. The system of claim 27, wherein the incident angle is greater than about 10°.

30. The system of claim 27, wherein the incident angle is greater than about 30°.

31. The system of claim 27, wherein the refractive index of the optical coupler is greater than the first index.

32. The system of claim 27, wherein the treatment beam source is configured to direct the treatment beam to the substrate through the optical coupler.

33. The system of claim 27, wherein the treatment beam produced by the treatment beam source has a wavelength different than that of the probe beam produced by the probe beam source.

34. The system of claim 27, wherein the treatment beam produced by the treatment beam source has a power greater than that of the probe beam produced by the probe beam source.

35. The system of claim 27, wherein the incident angle is less than the critical angle for an interface between the optical coupler and a material consisting essentially of fat and greater than the critical angle for an interface between the optical coupler and another material consisting essentially of one of muscle, blood vessels, and skin.

36. The system of claim 27, wherein the optical coupler is made of one of sapphire, fused silica, BK-7 glass, fint glass, germanium, and zinc selenide.

37. The system of claim 27, wherein the probe beam source is a diode laser, a helium neon laser, or a light emitting diode.

38. The system of claim 27, wherein the treatment beam source is a Nd:YAG laser, CTE:YAG laser, ErCr:YSGG laser, holmium laser, erbium laser, $CO_2$ laser, diode laser, or dye laser.

39. The system of claim 27, wherein the incident angle is selected such that when the probe beam is incident on the surface of the optical coupler configured to contact the substrate at the incident angle, the reflectance of the probe beam from an interface between the optical coupler and the portions of the substrate having the first index is at least twice the reflectance of the probe beam from an interface between the optical coupler and the portions of the substrate having the second index.

40. The system of claim 27, wherein the incident angle is selected such that when the probe beam is incident on the surface of the optical coupler configured to contact the substrate at the incident angle, the reflectance of the probe beam from an interface between the optical coupler and the portions of the substrate having the first index is at least four times the reflectance of the probe beam from an interface between the optical coupler and the portions of the substrate having the second index.

41. The system of claim 27, wherein the incident angle is selected such that when the probe beam is incident on the surface of the optical coupler configured to contact the substrate at the incident angle, the reflectance of the probe beam from an interface between the optical coupler and a material consisting essentially of fat is at least twice the reflectance of the probe beam from an interface between the optical coupler and a material consisting essentially of one of muscle, blood vessels, and skin.

42. The system of claim 27, wherein the incident angle is selected such that when the probe beam is incident on the surface of the optical coupler configured to contact the substrate at the incident angle, the reflectance of the probe beam from an interface between the optical coupler and a material consisting essentially of fat is at least four times the reflectance of the probe beam from an interface between the optical coupler and a material consisting essentially of one of muscle, blood vessels, and skin.

* * * * *